United States Patent
Gooding et al.

(10) Patent No.: US 11,562,493 B2
(45) Date of Patent: Jan. 24, 2023

(54) METHOD AND APPARATUS FOR GENERATING A UNIVERSAL ATLAS DATABASE

(71) Applicant: Mirada Medical Limited, Oxford (GB)

(72) Inventors: Mark John Gooding, Oxford (GB); Devis Peressutti, Oxford (GB); Paul Aljabar, Oxford (GB)

(73) Assignee: Mirada Medical Limited, Oxford (GB)

( * ) Notice: Subject to any disclaimer, the term of this patent is extended or adjusted under 35 U.S.C. 154(b) by 59 days.

(21) Appl. No.: 16/770,808

(22) PCT Filed: Dec. 10, 2018

(86) PCT No.: PCT/EP2018/084165
§ 371 (c)(1),
(2) Date: Jun. 8, 2020

(87) PCT Pub. No.: WO2019/121103
PCT Pub. Date: Jun. 27, 2019

(65) Prior Publication Data
US 2020/0334825 A1  Oct. 22, 2020

(30) Foreign Application Priority Data
Dec. 19, 2017 (GB) ..................... 1721257

(51) Int. Cl.
*G06T 7/149* (2017.01)
*G06T 7/12* (2017.01)
*G06T 7/00* (2017.01)

(52) U.S. Cl.
CPC ............ *G06T 7/149* (2017.01); *G06T 7/0012* (2013.01); *G06T 7/12* (2017.01);
(Continued)

(58) Field of Classification Search
CPC ............ G06T 2207/30004; G06T 2207/20128
See application file for complete search history.

(56) References Cited

U.S. PATENT DOCUMENTS 6,335,980 B1  1/2002 Armato et al.
7,584,080 B2 *  9/2009 Taylor .................... G06V 10/76
703/2
(Continued)

FOREIGN PATENT DOCUMENTS

CN       107093176 A1    8/2017
WO       2013040693 A1   3/2013
WO       WO-2016198568 A1 * 12/2016 ........... G06T 7/0014

OTHER PUBLICATIONS

Hongzhi Wang et al: "A learning-based wrapper method to correct systematic errors in automatic image segmentation: Consistently improved performance in hippooampus, cortex and brain segmentation", Neuroimage, Elsevier, Amsierdam, NL, vol. 55, No. 3, Jan. 5, 2011 (Jan. 5, 2011), pp. 968 . . . 985f.
(Continued)

*Primary Examiner* — Gandhi Thirugnanam
(74) *Attorney, Agent, or Firm* — Optimus Patents US, LLC

(57) ABSTRACT

A method (900) of generating an atlas for a universal atlas database (901) is provided. A new medical scan image (905) is provided. A universal auto-contouring operation (920) is performed on the medical scan image, to generate a set of universal contours (930) for the medical scan image. A local auto-contouring customisation operation (940) is performed on the medical scan image, to generate a set of local contours (950) for the medical scan image. The set of local contours is standardised (980) using a trained model to compensate for biases in the set of local contours, thereby creating a set of standardised global contours (985) for the medical scan image. The set of standardised global contours (985) and the medical scan image (905) can be added to the universal atlas database (901) as a new atlas, thereby expanding the set of atlases that are available in the universal atlas database.

13 Claims, 16 Drawing Sheets

(52) U.S. Cl.
CPC ............... *G06T 2207/20081* (2013.01); *G06T 2207/20128* (2013.01); *G06T 2207/30004* (2013.01)

(56) References Cited

U.S. PATENT DOCUMENTS

| | | | | |
|---|---|---|---|---|
| 7,995,813 | B2* | 8/2011 | Foshee | A61N 5/103 382/128 |
| 8,391,603 | B2* | 3/2013 | Tizhoosh | G06K 9/6253 382/128 |
| 9,361,701 | B2* | 6/2016 | Tizhoosh | G06T 7/12 |
| 9,704,243 | B2* | 7/2017 | Blumhofer | G16H 30/40 |
| 10,297,025 | B2* | 5/2019 | Magda | G06T 7/149 |
| 2003/0228042 | A1* | 12/2003 | Sinha | G06T 7/344 382/218 |
| 2008/0154565 | A1* | 6/2008 | Florin | G06K 9/6256 703/11 |
| 2009/0226060 | A1* | 9/2009 | Gering | G06T 7/174 382/128 |
| 2010/0266170 | A1* | 10/2010 | Khamene | G06T 7/149 382/128 |
| 2010/0322489 | A1* | 12/2010 | Tizhoosh | G06T 7/12 345/157 |
| 2011/0216954 | A1* | 9/2011 | Sundar | G06T 7/11 382/294 |
| 2013/0040693 | A1 | 2/2013 | Tizhoosh et al. | |
| 2014/0161329 | A1* | 6/2014 | Tizhoosh | G06T 7/149 382/128 |
| 2014/0247977 | A1* | 9/2014 | Han | G06K 9/6292 382/159 |
| 2014/0341449 | A1* | 11/2014 | Tizhoosh | A61B 8/565 382/128 |
| 2015/0238158 | A1* | 8/2015 | Zhou | G06V 10/44 382/131 |
| 2018/0096478 | A1* | 4/2018 | Zhang | G16H 50/20 |
| 2018/0174302 | A1* | 6/2018 | Gooding | G06T 7/174 |
| 2020/0334825 | A1* | 10/2020 | Gooding | G06T 7/149 |

OTHER PUBLICATIONS

Hongzhi Wang et al: "Multi-atlas segmentation with joint label fusion and corrective learning•an open source implementation", Frontiers in Neuroinformatics. vol. 7:27t Nov. 22, 2013 (Nov. 22, 2013), pp. 1 . . . 12, XP055583433, DOI: 10.3389/fninf.2013.00027.
Gregoire, Vincent et al; Delineation of The Neck Node Levels for Head and Neck Tumors: A 2013 update. DAHANCA, EORTC, HKNPCSG, NCIC CTG, NCRI, RTOG,TROG consensus guidelines; www.thegreenjournal.com; Radiotherapy and Oncology; Oct. 31, 2014; pp. 1-10.
EPO Article 94(3) Communication; Corresponding EPO Application Serial No. 18819068.0; dated Oct. 26, 2022.

* cited by examiner

METHOD AND APPARATUS FOR GENERATING A UNIVERSAL ATLAS DATABASE

FIELD OF THE INVENTION

This invention relates to the fields of medical imaging and medical image processing. In particular, the invention relates to the standardisation of data in automatic image contouring.

BACKGROUND OF THE INVENTION

Various technologies can be used to acquire internal images of human anatomy. Typically, internal images are acquired with a Computed Tomography (CT) scan. However, other imaging modalities, such as Magnetic Resonance (MR), may be used. Lower accuracy applications may rely on ultrasound scans. The raw images acquired using CT and MR scanners can be enhanced and analysed to provide very valuable information, such as accurate measurements of structures in the images.

Measuring and analysing structures in CT or MR images may provide information that serves as one input to a variety of subsequent tasks. One such task may be part of research. In some research projects, there is a need for accurate measurement or delineation of structures in CT or MR images to assess individual organs. Alternatively, research may focus on analyses of differences between organs across a population of different individuals.

In a further alternative, the subsequent tasks may include work by a radiation oncologist. A radiation oncologist may take images, and use them as an input to for example, preparing for treatment of a patient. The delineation of tumours and target volumes in CT or MR images enables a radiation oncologist to better discriminate between organs-at-risk (OARs) and other areas, such as healthy tissue. The radiation oncologist can then develop a 'planning' image, with the aim of sparing healthy tissues in subsequent actions.

When a radiation oncologist reaches the point of planning interventions in radiotherapy, (s)he may use planning software to calculate a treatment plan. That plan typically maximises radiation dose to the target volume and tumour, while minimising dose to the surrounding healthy tissues. Accurate delineation and targeting is very important during treatment planning. This example serves to illustrate the value of any input that can be provided by the enhancement, analysis and interpretation of original CT and MR images.

Contouring

The process of delineating structures within an image is also known as 'contouring'. The term contouring may be used to indicate the process of delineation in either 2D or 3D, to define the boundary of an anatomical structure. Similarly, the term 'auto-contouring' may be used to indicate the process of producing a contour automatically, and this is discussed further in a separate section below.

Medical scan images of anatomical structures are typically approved by trained radiation oncologists, dosimetrists or radiographers for subsequent treatment planning. Approved anatomical structures may be referred to as 'gold-standard contours'. Gold-standard contours are therefore contours that have been curated and approved by expert clinicians as having high quality. Gold-standard contours are sometimes also termed 'ground-truth' contours. An 'atlas' comprises the pairing of an image and the gold-standard contours for that image. Gold-standard contours are often created in accordance with a given set of contouring guidelines. One such set of contouring guidelines is the 'RTOG' guidelines at: http://www.rtog.org/CoreLab/ContouringAtlases.aspx The atlases, each comprising gold-standard contours and a corresponding image, can be stored in a database, thereby providing a database of atlases. The atlases are then available for various uses with images that are obtained subsequently. Atlases in the database act as an accumulated store of information, which may greatly improve the processing of subsequent, newly acquired images. Atlases are used to facilitate the contouring of newly acquired patient images, which typically are not images of the same patient as the image from which the atlas and its gold standard contours were derived.

Manual contouring of a medical scan image by a human operator is time consuming, and subject to variability in delineating the anatomical structures. Such variability is due to intra- and inter-operator variation, and due to protocol variations between different medical institutions, or different departments in one medical institution. In fact, different institutions, or even different groups within an institution, may have different contouring guidelines for OARs. Differences between contouring guidelines can exist because the different institutions may subsequently use different protocols for research evaluation or at the stage of planning subsequent treatment. For example, a protocol used at institution A may not be usable at institution B. Within the same institution, different protocols may also be employed, depending for example on the stage and location of a structure such as a tumour.

As a consequence, there may be variations in the gold-standard contours that are generated for a single medical scan image. These variations depend on factors such as the institution/department guidelines and protocols, the state of an organ in the image, and individual operators who process the images.

Given the required amount of time and the inherent variability in defining a gold-standard, contouring represents one of the institutional bottlenecks in the processing of CT and MR images. Delays in image processing may lead to delays in publishing research, or in other subsequent work. Very accurate contours may need to be provided, and such accuracy may take time with known systems.

Auto-Contouring

Auto-contouring methods have been developed. Auto-contouring methods aim, at least in part, to overcome the issues described above.

Auto-contouring methods may generate contours using different technologies. One example of such technologies involves the use of previously delineated cases. Another example of such technologies involves developing model-based approaches. The results of auto-contouring may still require manual editing to account for inaccuracies, and to make the results adhere to an institution or department's contouring guidelines, i.e. to provide a suitable input to subsequent protocols that are in use at that institution or department. In this case, the editing time for the results of auto-contouring can be significantly less than the time that would be required to manually delineate the entire image volume.

The term 'auto-contouring' is a collective description for various underlying approaches. The underlying technological approaches may actually differ widely between systems. These variations in underlying technological approaches are as reported in the literature, see for example reference [1] in the list of references at the end of this 'Background' section.

In generating any auto-contouring method, the organs within one or more example medical images, normally CT images, are carefully delineated by a clinical expert to generate gold-standard contours following specific contouring guidelines. This combination of a medical image and gold-standard structures is the 'atlas'.

FIG. 1 illustrates a generic auto-contouring method. Method 100 in FIG. 1 is a generic implementation of a known auto-contouring method. FIG. 1 is partly a high-level flowchart and partly a schematic diagram.

At step 105, a new image is acquired, for example by a CT or MR scan. The aim of method 100 is to contour the new image. At step 120, one of several auto-contouring methods may be applied. Training atlas database 101 provides at least one training atlas as an input to step 120.

Each of subsequent FIGS. 2-4 provides more detailed steps for one way of carrying out the auto-contouring method of step 120. Thus, in FIG. 1, the step 120 should be seen as representing any of the methods of FIGS. 2-4. Regardless of the algorithm used in step 120, step 120 will provide estimated contours 130. The estimated contours 130 will reflect the contouring style described by the training atlas database 101.

In the case of commercial systems, users typically cannot modify the auto-contouring algorithm that is used in step 120. However, the users might be able to access/modify the training atlas database 101. Examples of such modification might be adding new atlases, in atlas-based contouring.

Traditional approaches to auto-contouring simply rely on the image intensity values and image intensity gradient values. More recent approaches incorporate prior-knowledge about the appearance and shape of the structure that is to be contoured.

Three main methodological approaches amongst these prior-knowledge-based methods are described below. These are 'atlas-based' contouring, statistical models of shape and appearance, and machine learning. An example of atlas-based contouring is shown in FIG. 2. An example of shape-model based autocontouring is shown in FIG. 3. An example of machine learning-based auto-contouring is shown in FIG. 4. The methods of FIGS. 2-4 may be used alone, or alternatively may also be used in combination.

Atlases are used to generate any of the auto-contouring methods described in FIGS. 2-4 below. However, atlases are very widely applicable in image interpretation, and are used for other actions than just autocontouring. Thus, in the remainder of this description and the figures, the use of an atlas in any step should not be taken necessarily to imply that atlas-based autocontouring is occurring.

Atlas-Based Auto-Contouring

In the remainder of the present application, an atlas database is considered as storing a pool of atlases that are available for selection. Each atlas in the pool of atlases comprises a medical image dataset and at least one defined structure delineating at least one object (e.g. region or organ) within the medical image. Typically, the pool of candidate atlases comprises a large number of candidate atlases, for example potentially hundreds or even thousands of candidate atlases.

When a new patient image is to be contoured, the atlas image/s is/are aligned to the new patient image using deformable image registration. The structures shown in the atlas are then mapped from the atlas to the new patient image, using the estimated deformation field.

Where multiple atlases are available, multiple estimates for the boundary of each organ can be obtained for the patient image. These would be merged into a consensus structure. If contours from multiple atlases have been warped to one new CT image, then each one represents a different estimate of the required contour. In this case, it is possible to obtain the consensus structure, i.e. a single consensus estimate for the required contour. This can be achieved by averaging the warped contours. Alternative approaches are to take a 'majority vote' of the labels that the contours provide at each location, or to use some more advanced statistical method.

Atlas-based contouring methods are typically limited by the amount of deformation that the registration is able to represent correctly, and by the number and quality of the atlases. Atlas contouring is widely reported in the literature, for example references [2] and [3].

FIG. 2

FIG. 2 shows an example implementation of a generic atlas-based auto-contouring method 200. Method 200 is one example of an implementation of method step 120 of FIG. 1. The aim of method 200 is to contour a new image. At step 210, a new image is acquired, for example by a CT or MR scan, for contouring. At step 220, one or more atlases is selected from training atlas database 201.

At step 230, one or more atlases are brought into registration with the CT image to be contoured. The registration requires a transformation, in order to register the atlas to the CT image that is to be contoured. That transformation is derived, either iteratively or directly, as part of step 230. The transformation is saved and used in step 240.

At step 240, the gold-standard contours are warped from the atlas coordinate system to the coordinate system of the CT image. This warping is done using the transformations estimated at step 230.

At step 250, if more than one atlas was used from step 220, then a consensus contour is generated from the warped contours.

At step 260, the contours can be returned to the user. Thus the CT image that served as the starting point of method 200 at step 210 has been auto-contoured, and is ready for subsequent use. This use may be, for example, to evaluate a medical image for research purposes, or as an input to subsequent preparations for radiotherapy.

At step 220, one or more atlases were selected. However, the selection of the one or more atlases can be undertaken during a training phase, prior to the start of the auto-contouring method 200 on the particular CT image that was acquired at 210.

Statistical Models of Shape and Appearance

Statistical models of shape and appearance aim to capture the statistical variations in shape and appearance of an anatomical structure(s) within a given training dataset of atlases. At training time, gold-standard structures and the corresponding CT images need to be available to develop a statistical model, just as for atlas-based contouring. Therefore, it is necessary to build such a training dataset of atlases following specific contouring guidelines. As these methods model the variation in shape and appearance of the training data, their performance is highly dependent on the size and quality of the training atlas database. For instance, the literature in references [4]-[6] covers some types of statistical shape and appearance models.

FIG. 3

FIG. 3 illustrates a generic statistical shape and appearance auto-contouring method. FIG. 3 shows an implementation of a shape and appearance model-based auto-contouring method 300. Method 300 is another example of an implementation of method step 120 of FIG. 1.

Atlas database 301 provides a source of atlases. The remainder of method 300 is divided into first section 304, which includes the training steps, and second section 306, which includes the testing steps.

Within first section 304, in the training steps, the anatomical variability in shape and size of training ground-truth contours is described using statistical techniques. One example of such a statistical technique is 'Principal Component Analysis'. The image appearance of the training CT images, from atlas database 301, can also be used when generating the statistical model. At the end of training, a statistical shape model will be generated and used for contouring unseen CT images. Within first section 304:

(i) Step 310 comprises retrieving training CT images and corresponding gold-standard contours from atlas database 301.

(ii) Step 320 comprises generating a statistical model correlating image appearance with organ shape.

(iii) Step 330 comprises returning a statistical shape model. The statistical shape model then serves as an input to second section 306, including the testing steps.

Within second section 306, during testing, the statistical shape model will be fitted to an unseen, new CT image. At the end of the testing, the resulting contours are returned to the user. Within second section 306:

(i) Step 340 comprises acquiring a CT image to be contoured. The acquisition may be simply retrieving the CT image from a database, or may involve the steps of operating a CT, MR or other scanner to acquire the image.

(ii) Step 350 comprises fitting the statistical shape model from step 330 to the CT image to be contoured.

(iii) Step 360 comprises returning the contours to a user.

Machine Learning

Machine learning refers to a set of mathematical and statistical techniques for learning underlying patterns in training data. 'Deep learning' is one example of machine learning.

Unlike statistical shape and appearance models, machine learning does not explicitly enforce constraints on shapes, or assume that they have particular statistical distributions. Instead, machine learning approaches seek to learn such distributions automatically. For this reason, machine learning methods tend to model variation better than statistical shape models. However, machine learning methods remain limited by the size and content of the training data. Similarly, such approaches need a carefully curated atlas database. The atlas database must have carefully contoured gold-standard cases, which have been contoured to a consistent set of contouring guidelines. Some examples of machine learning methods for auto-contouring in the literature are shown in references [7]-[9].

FIG. 4

FIG. 4 illustrates a generic machine learning auto-contouring method 400. Atlas database 401 provides a source of atlases. The remainder of method 400 is divided into first section 404, which includes training steps, and second section 406, which includes testing steps.

Within first section 404, a mathematical model with trainable parameters is optimised to correlate image features extracted from training CT images and their gold-standard contours. At the end of the training of first section 404, the mathematical model is optimised to predict contours of CT image that was to be contoured. Within first section 404:

(i) At step 410, training CT images and corresponding gold-standard contours are retrieved from atlas database 401.

(ii) At step 420, imaging features are extracted from the training medical image scan(s).

(iii) At step 430, a mathematical model with trainable parameters is chosen to correlate imaging features to gold standard contours.

(iv) At step 440, the model parameters are optimised. This optimisation continues until convergence of the training objective function has been achieved.

(v) At step 450, the model is ready for use and is returned to the user.

Within second section 406, during testing, the trained model will be run on an unseen, new CT image. At the end of the testing, the resulting contours are returned to user. During testing, the unseen, new CT image is provided as the input to the trained machine learning model, and contours are generated as the output. Within second section 406:

(i) Step 460 comprises acquiring a CT image to be contoured. The acquisition may be simply retrieving the CT image from a database, or may involve the steps of operating a CT, MR or other scanner to acquire the image.

(ii) Step 470 comprises running the trained model on the CT image to be contoured. The result comprises contours.

(iii) Step 480 comprises returning the contours to a user.

Comparing FIGS. 1 and 4, it is clear that steps 460, 470 and 480 of method 400 correspond respectively to steps 105, 120 and 130 respectively of method 100.

The Performance of Auto-Contouring

The performance of auto-contouring methods is currently hampered by the inherent variation in the definition and execution of the gold-standard contours. The gold-standard contours form the data that is used to build the auto-contouring methods. In practice, in known systems, this has limited the accuracy and robustness of auto-contouring methods.

'Accuracy' typically measures the degree of agreement between the automatic contours and the manually defined gold-standard. 'Robustness' ensures that accurate results are achieved regardless of random and systematic biases in the particular medical image case. Examples and sources of these biases are imaging artefacts, imaging scanner manufacturer, and acquisition protocols.

A robust method may generalize well, in that it provides reasonable average accuracy across a range of institutions. However, a robust method may still fail to produce contours that meet the contouring guidelines for OARs of specific clinical departments or operators. Conversely, an auto-contouring method that is carefully tailored to be accurate for a specific set of contouring guidelines, to provide a set of contours that is suitable for a subsequent treatment planning protocol, is likely to fail drastically when applied to a different set of contouring guidelines. A robust model could be generated using a database populated by multiple institutions. However it is paramount that such a database of atlases is coherently and similarly defined.

All the auto-contouring methods mentioned above can model the variation of the population of images in the atlases available at training time, or, in the case of atlas-based auto-contouring, the variation represented with the selected atlas set. However, given an auto-contouring model generated using a specific training dataset developed to just one contouring standard, an operator will be required to adapt the resulting contours to their institutional/departmental guidelines. Once again, this adaptation is a source of delay, and may introduce further inaccuracies.

To overcome this limitation, a local contouring method to correct for systematic errors introduced by a universal auto-contouring method has been proposed in the literature.

See reference [10]. In Reference [10], an enhanced approach is provided, which will now be described in detail.

FIG. 5

FIG. 5 illustrates a known local customisation method of auto-contouring a medical scan image. FIG. 5 shows the use of a local contouring method in accordance with [10]. Method 500 shown in FIG. 5 uses a machine learning technique. The method 500 is referred to as a 'local' method.

The technique of method 500 is used to learn to correct for systematic biases introduced by a universal auto-contouring method that uses pre-determined image, contextual and spatial features. In this case, the universal auto-contouring method is not accessible to the operator and cannot be updated or modified. The universal auto-contouring method could be any of the auto-contouring systems described above.

A universal training atlas database 501 holds training atlases. A local atlas database 510 holds local atlases that are appropriate to a local context, such as a particular institution or medical department.

The method 500 starts when there is a CT image 505 to contour. However, method 500 could start with an MR or other image. At step 520, a universal auto-contouring method operates on the CT image acquired at 505. The universal auto-contouring method applies a contouring style from universal training atlas database 501 to CT image 505. The result of step 520 is a set of estimated contours 530.

At step 540, the estimated contours 530 are then fed to a local contouring method at 540. Local contouring method 540 learns from local atlas database 510, to correct the estimated contours 530 for systematic biases introduced by step 520. The result is a set of corrected contours 550. The resulting corrected contours 550 are then available to the local operator. At step 560, the operator edits and finally approves the corrected contours.

The inventors have realised that, potentially, method 500 would allow the incorporation of the approved, corrected contours and the CT image back into the local atlas database 510. However, such incorporation of the approved corrected contours is not shown in reference [10].

Thus method 500 provides edited and approved, corrected contours for the CT image 505 that was the starting input to method 500. Those contours are of particular use for just the CT image 505 itself. However, in addition, method 500 potentially provides a way to expand local atlas database 510. If method 500 were repeated for many different initial images such as CT image 505, then over time the local atlas database 510 could then provide a reservoir of images. From those images it would be possible to learn how to correct the estimated contours of subsequent images 505 for systematic biases introduced by step 520.

Such an approach to expanding the local atlas database 510 shown in FIG. 5 would lead, over time, to the creation of a more useful reservoir of images. Those images could then be used within the institution of their origin.

More generally, all of the types of auto-contouring detailed in FIGS. 1-5 above would benefit from using a larger dataset in the atlas database. This is true, whether the dataset is to be used to train a model, or to be treated as a set of accepted atlases from which to select a particular subset. However, while method 500 would potentially allow expansion of the local atlas database 510, the inventors have realised that there would be significant issues that would prevent the approved local contours and corresponding CT image 505 being added to the universal atlas database 501, as explained in the following.

In general, whenever a larger dataset can be made available, most of the methods used for universal auto-contouring would be improved. This is true whether the data are used to train a model, or are treated as a repository from which to select atlases for a multi-atlas contouring step. As described earlier, the inventors have considered that locally curated contouring results could be used to update the local database in method 500, and this would lead to local benefits. However, the inventors have recognised further advantages that could also be achieved if the different centres could all provide their quality assessed results to expand the universal atlas database 501. An expanded universal atlas database 501 would improve the universal contouring standard for all centres to then use. There are however, issues that would arise when using approved local contours 560, and the corresponding CT images 505, to expand the universal database 501, as explained in the following.

Returning to method 500, reference [10] proposed a local auto-contouring method 540 to correct for systematic contouring errors produced by a universal auto-contouring method 520. The universal method can be any of the auto-contouring algorithms described in FIGS. 2-4. The method 500 extends to the local auto-contouring method learning to adapt the contours generated by the universal auto-contouring method to the local guidelines of the institution/department. This part of the process is achieved in step 540 and is described in further detail in FIG. 6. At training time, method 500 is provided with both universal and local contours. It then optimises the parameters of a machine learning algorithm to adjust the output of each set of estimated contours 530, i.e. each universal contour set, so that it matches the corresponding local set as closely as possible. Reference [10] actually proposed two possible implementations of the algorithm, although the aim of each is the same.

FIG. 6

FIG. 6 illustrates an implementation of a known local customisation method shown in FIG. 5. Method 600 of FIG. 6 illustrates a known training implementation, for a local auto-contouring method.

In order to train a local auto-contouring method, the medical image scans, the associated local gold standard contours and the contours generated by the universal auto-contouring system will be considered. Imaging, spatial and contextual features are extracted from the images and from the generated universal contours. Reference [10] proposed two methods:

(i) Two machine learning classifiers are trained using the extracted features. The first classifier estimates voxels which are mis-labelled by the universal auto-contouring method, while a second classifier then re-labels the voxels identified by the first classifier.

(ii) One machine learning classifier is trained using the extracted features to re-label all voxels in a pre-defined region-of-interest.

With method 600, local atlas database 610 provides local gold standard contours. Universal atlas database 620 provides universal auto-contouring contours.

At step 630, a training medical image scan, the local gold standard contours and the universal auto-contouring contours are retrieved. Step 630 involves the retrieval of the corresponding contours, i.e. local gold-standard and estimated universal contours, from databases 610 and 620 associated to the training CT image.

At step 640, method 600 finds any voxels that had been mis-labelled by the universal auto-contouring method 520, compared to the local gold-standard contours.

At step 650, method 600 extracts imaging and contextual features from the training images and the universal contours. At step 660, an AdaBoost algorithm is trained to correlate imaging and contextual features with correct labels. At step 670, the trained model is returned for subsequent use. FIG. 7

The problems recognised by the inventors in any attempt to expand the universal atlas database, i.e. dataset of training atlases for the universal auto-contouring method, can be understood more clearly from FIGS. 7 and 8. Datasets need to be consistent to be effective, and this can be difficult to achieve with known approaches.

FIG. 7 illustrates the outcome of applying a known local customisation method of auto-contouring to a medical scan image. FIG. 7 provides a visual example of the contouring style of the universal and local methods.

For example, in FIG. 7 a new medical scan image, 701, is to be contoured. The contouring is to use contours 710 that have been provided to the contouring standard of images in the universal atlas database 501, i.e. the new medical scan image is to be contoured by a method trained on or using an atlas database 501. The contours shown at 710 are an example of the contouring style of the universal auto-contouring method, derived by using the universal training atlas database 101. The universal auto-contouring method can be any of the methods in FIGS. 2-4.

The process results in contours that are schematically illustrated as the image 720. Thus the contours shown at 720 are contours that are generated by the universal auto-contouring method for medical image scan 701.

By comparing the various contours of the image 720 with the original medical scan image 701, it is possible to recognise the effects of the contouring standard using the universal auto-contouring method 520.

The contours shown at 730 are then the results of a local method A trained on a local atlas database from institution/department A. The contours reflect the contouring style of institution/department A. The contours shown at 740 are the results of another local method B trained on a local atlas database from institution/department B. The contours reflect the contouring style of institution/department B Considering again step 540 of FIG. 5, a local auto-contouring method has been applied to image 720. The local method has corrected the contours for different destination institutions A and B. The result of this correction step is image 730 for institution A, and image 740 for institution B.

As shown at step 560 of FIG. 5, institutions A and B can edit images 730 and 740, respectively, if required, and accept the contours shown in each of images 730 and 740. Each of institutions A and B can choose to contribute its image 730, 740 to their corresponding local atlas databases 510. However, it is clear that one image 720 has been altered very differently at institution A, providing image 730, than at institution B, providing image 740.

FIG. 8

FIG. 8 illustrates problems that the inventors have recognised would occur with known systems, if an attempt were made with known systems to use the contouring results approved at a local level to update the universal atlas database 501. With known systems, any such attempt would lead to difficulties that can be understood with reference to the specific example illustrated in FIG. 8.

In FIG. 8, a further medical scan image 801 is to be contoured. If a locally approved contour and CT image scan 730 were previously added to the universal atlas database and used to update the universal auto-contouring system, the universal contouring standard would be affected as shown in 810. The contouring standard 810 is biased towards image 730 in FIG. 7 that is valid for institution A. This can be seen by comparing image 810 of FIG. 8 with image 730 in FIG. 7.

Medical scan image 801 is then contoured using the updated universal standard 810, which results in the contours shown in image 820. However, the correction system that had earlier been tuned to adjust for the systematic universal errors, based on the local atlas 510, is no longer appropriate, because the universal contouring standard 810 has changed. Therefore, as illustrated in FIG. 8, the system results in images 830 and 840 for institutions A and B. Each of images 830 and 840 would not fulfil the local guidelines and would require yet more correction.

FIG. 8 thus illustrates the outcome of known method, when a universal atlas database is used to contour new data. However, the method 800 shows what would happen if the universal atlas database were to be expanded with examples that were customised for and approved by a specific local centre. The processed images that are shown in FIG. 8 demonstrate that, with known approaches, any attempt to provide additional data by adding more images into the universal atlas database 501 would actually degrade the performance of the system. FIG. 8 thus provides an overview of problem that the present invention seeks to solve.

Reviewing each set of contours in FIG. 8 in more detail, 801 shows a new medical scan image to be contoured. Contours 810 are generated from an atlas, by local auto-contouring method A, and are approved by users of institution/department A. If atlases from institution A are used to update the universal auto-contouring system, a bias towards the contouring style of that institution is introduced.

Contours 820 are generated by the universal auto-contouring method, using the atlases added from institution/department A. The contouring style is different from the original universal method as shown in 710.

Contours 830 are then generated by applying a different local auto-contouring method A on contours 820. The bias introduced by 810 propagates to the local contouring system A. These contours might not comply with the guidelines of institution/department A, due to the introduced bias.

Contours 840 are generated by applying a different local auto-contouring method B on contours 820. The bias introduced by 810 propagates to the local contouring system B. These contours might not comply with the guidelines of institution/department B, due to the introduced bias.

The contours generated by the local contouring methods could be used to update the database of local atlases only. However, with known approaches, the contours generated by the local contouring methods cannot be used to update the universal training database used to generate the universal auto-contouring system, because they introduce biases towards institutional/departmental guidelines.

REFERENCES

[1]: Sharp, G. et al. "*Vision 20/20: perspectives on automated image segmentation for radiotherapy*", Medical Physics, 41, 050902, 2014.

[2] Han, X., et al. "Atlas-based auto-segmentation of head and neck CT images." Medical Image Computing and Computer-Assisted Intervention—MICCAI 2008. Springer Berlin Heidelberg, 2008. 434-441.

[3] Ramus, L., and Malandain, G. "Multi-atlas based segmentation: Application to the head and neck region for radiotherapy planning." MICCAI Workshop Medical Image Analysis for the Clinic-A Grand Challenge. 2010.

[4] Taylor, C. J., et al. "Constructing a statistical shape model from two-dimensional or three-dimensional data", U.S. Pat. No. 7,584,080 B2, Imorphics Ltd., 2009.
[5] Cootes, T. F., et al. "Active appearance models", IEEE Transactions on Pattern Analysis and Machine Intelligence, vol 23, 2011.
[6] Khamene, A., et al. "Methods and systems for fully automatic segmentation of medical images", Siemens Corporate Research Inc., US 2010/0266170 A1, 2010.
[7] Florin, C., et al. "Automatic organ detection using machine learning and classification algorithms", Siemens Corporate Research Inc., US 2008/0154565 A1, 2008
[8] Montillo, A., et al. "Entangled decision forests and their application for semantic segmentation of CT images", Proceedings of the Information Processing in Medical Imaging, vol 22, 184-196, 2011
[9] Fritscher, K., et al. "Deep neural networks for fast segmentation of 3D medical images", MICCAI 2016, pp 158-165, 2016.
[10] Wang, H., et al. "*A learning-based wrapper method to correct systematic errors in automatic image segmentation: Consistently improved performance in hippocampus, cortex and brain segmentation*", Neuroimage, vol 55, 968-985, 2011.

SUMMARY OF THE INVENTION

The method and apparatus for medical imaging builds a consistent dataset for automatic contouring systems, for use in a universal atlas database. The dataset for automatic contouring systems is able, after suitable processing to use data generated according to local standards, after suitable processing of the data generated according to local standards in accordance with the invention. These local standards can include institutional variation in image acquisition protocols, treatment planning protocols, contouring guidelines and inter-operator variations.

The approach in the present application enables a standardised auto-contouring solution to be deployed more effectively. This is even the case when multiple institutions are involved, employing different protocols for treatment planning and with different contouring guidelines for OARs.

Thus the disclosed invention addresses the problem of how to build such a consistent atlas dataset within a multi-institution environment. In such an environment, operators are still able to contour to different standards for their own use in the local institution, but they can also contribute to expansion of the universal dataset. Such expansion of the universal dataset in a universal atlas database is to the benefit of all institutions that have access to the universal atlas database. The present invention concerns a method and system for providing a greater degree of standardisation of the data that is available for use in auto-contouring methods.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

The present invention will now be described with reference to the drawings specified above. However, it will be appreciated that the present invention is not limited to the specific embodiments herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated below, for the understanding and appreciation of the underlying concepts of the present invention.

DETAILED DESCRIPTION OF THE PREFERRED EMBODIMENTS

In accordance with an embodiment of the invention, a method of generating an atlas for a universal atlas database is provided. The method comprises providing a medical scan image, and performing a universal auto-contouring operation on the medical scan image to generate a set of universal contours for the medical scan image. The method further comprises performing a local auto-contouring customisation operation on the medical scan image, to generate a set of local contours for the medical scan image. Then the method standardises the set of local contours, using a trained model to compensate for biases in the set of local contours, thereby creating a set of standardised global contours for the medical scan image.

The medical scan image and the set of standardised global contours for the medical scan image may then be added to the universal atlas database as an atlas. Furthermore, a local atlas may also be added to the local atlas database, the local atlas comprising the medical scan image and the set of local contours, after the approval or editing of the set of local contours.

FIG. 9

Figure 9:
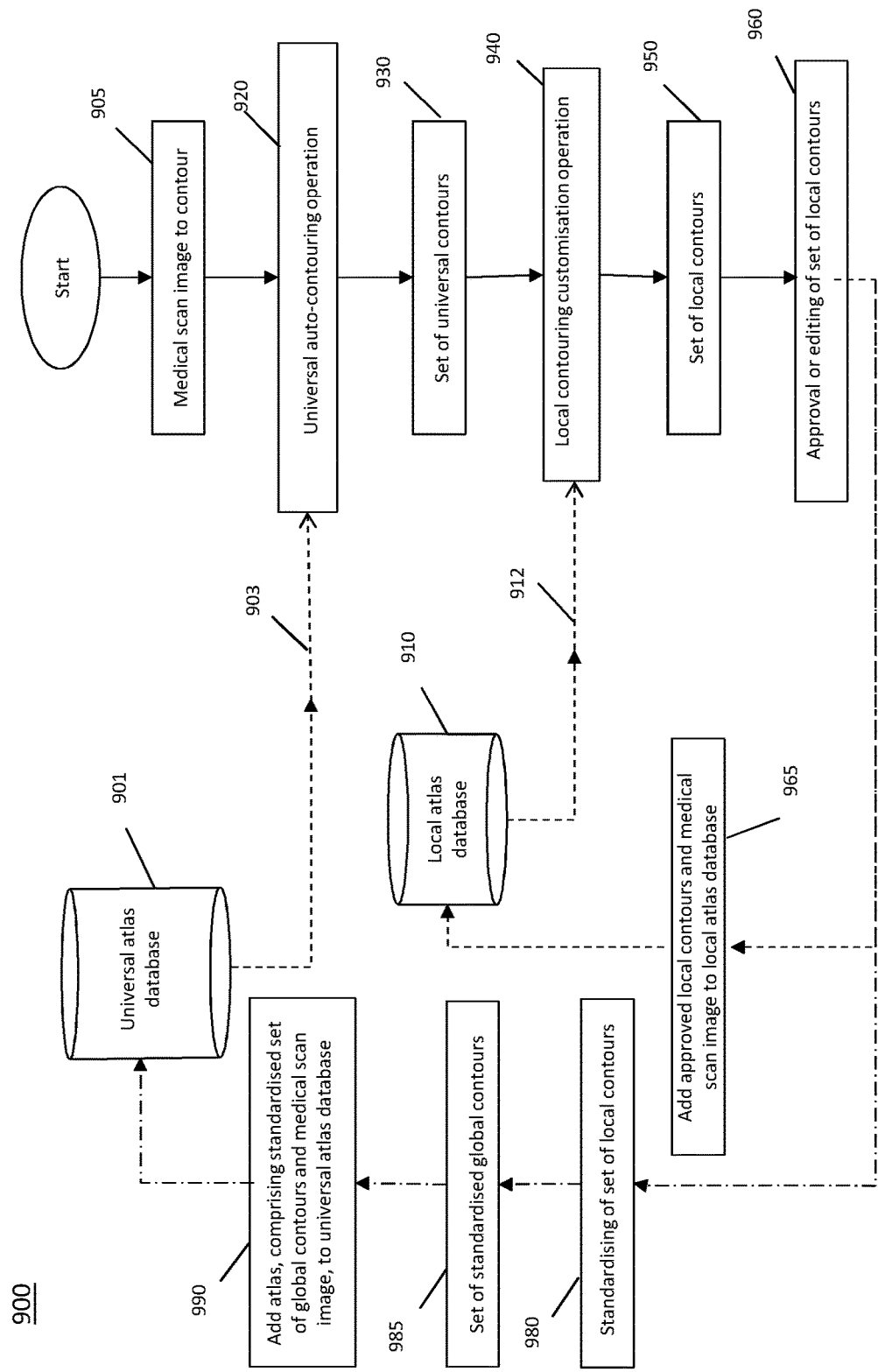
FIG. 9 illustrates a method in accordance with an embodiment of the invention.

FIG. 9 illustrates a method in accordance with an embodiment of the invention. In the method 900 of FIG. 9, multiple databases of atlases are available. Universal atlas database 901 provides an initial database of atlases of carefully curated data. The data comprises medical image datasets, each dataset comprising a medical scan image with at least one defined structure delineating at least one object, e.g. a region or organ, within the medical image. Each medical image dataset in universal atlas database 901 has been carefully curated according to specific contouring guidelines. Universal atlas database 901 may comprise thousands of atlases.

There may be one universal atlas database 901. The contents of the universal atlas database 901 may be available to many different institutions, which may be spread across a country or the globe. Within each institution, such as a medical research centre or an imaging centre, there may be multiple departments that have access to the universal atlas database 901.

Universal atlas database 901 may be generated by means of a standardised contouring method, as for instance defined by international contouring guidelines. We refer to this database as the 'universal' atlas database because of the universal standards with which its contents have been prepared, and also because its contents may have represented contributions that have come from many different local institutions. Universal atlas database 901 serves to eliminate any institutional/contouring protocol variation, but does capture patient population and imaging protocol variation.

Also shown in FIG. 9 is just one local atlas database 910. Local atlas database 910 may be one of many local atlas databases, which may each be held at different sites dispersed across the globe. Each local atlas database represents the gold-standard contours available to each institution/department. Thus the atlases in the local atlas database 910 describe the variations that are specific to the institutional/departmental guidelines. So a medical research centre or an imaging centre may have one or more local atlas databases 910, in addition to a link that allows access to atlases from the universal atlas database 901. Typically, one or more local atlas databases 910 are available per clinical institution.

Method 900 starts with the provision of a new medical scan image 905 that is to be contoured. A universal auto-contouring operation 920 is performed on the medical scan image 905. The universal auto-contouring operation 920 generates a set of universal contours 930 for the medical scan image 905.

Universal atlas database 901 may be used to assist with or to implement universal auto-contouring step 920. The universal auto-contouring operation 920 may be performed on the medical scan image 905 with input, shown at 903, from the universal atlas database 901. The input from the universal atlas database 901 to the universal auto-contouring operation 920 may comprise a stored atlas from the universal atlas database 901. In some implementations universal atlas database 901 may provide more than one stored atlases for use in universal auto-contouring operation 920. Alternatively, the input from the universal atlas database 901 to the universal auto-contouring operation 920 may comprise a set of variations between a plurality of atlases stored in the universal atlas database 901.

The universal auto-contouring operation 920 may be an atlas-based operation. However, universal auto-contouring operation 920 may alternatively or additionally use a shape/appearance model, a machine learning approach, or a deep learning algorithm.

Universal auto-contouring step 920 leads to an estimated set of universal contours 930, for example for any OARs for the new medical scan image 905. The set of universal contours 930 will reflect the contouring guidelines that were used to create the atlases in the universal atlas database 901.

The next step is to customise the universal contours to the specific institutional/departmental guidelines. To do this, a local auto-contouring customisation operation 940 is performed on the medical scan image 905. The local auto-contouring customisation operation 940 generates a set of local contours 950 for the medical scan image 905. Local atlas database 910 may supply one or more local atlases for the local auto-contouring customisation operation 940, i.e. atlases that originate from the institutional/departmental local atlas database 910.

Figure 6:
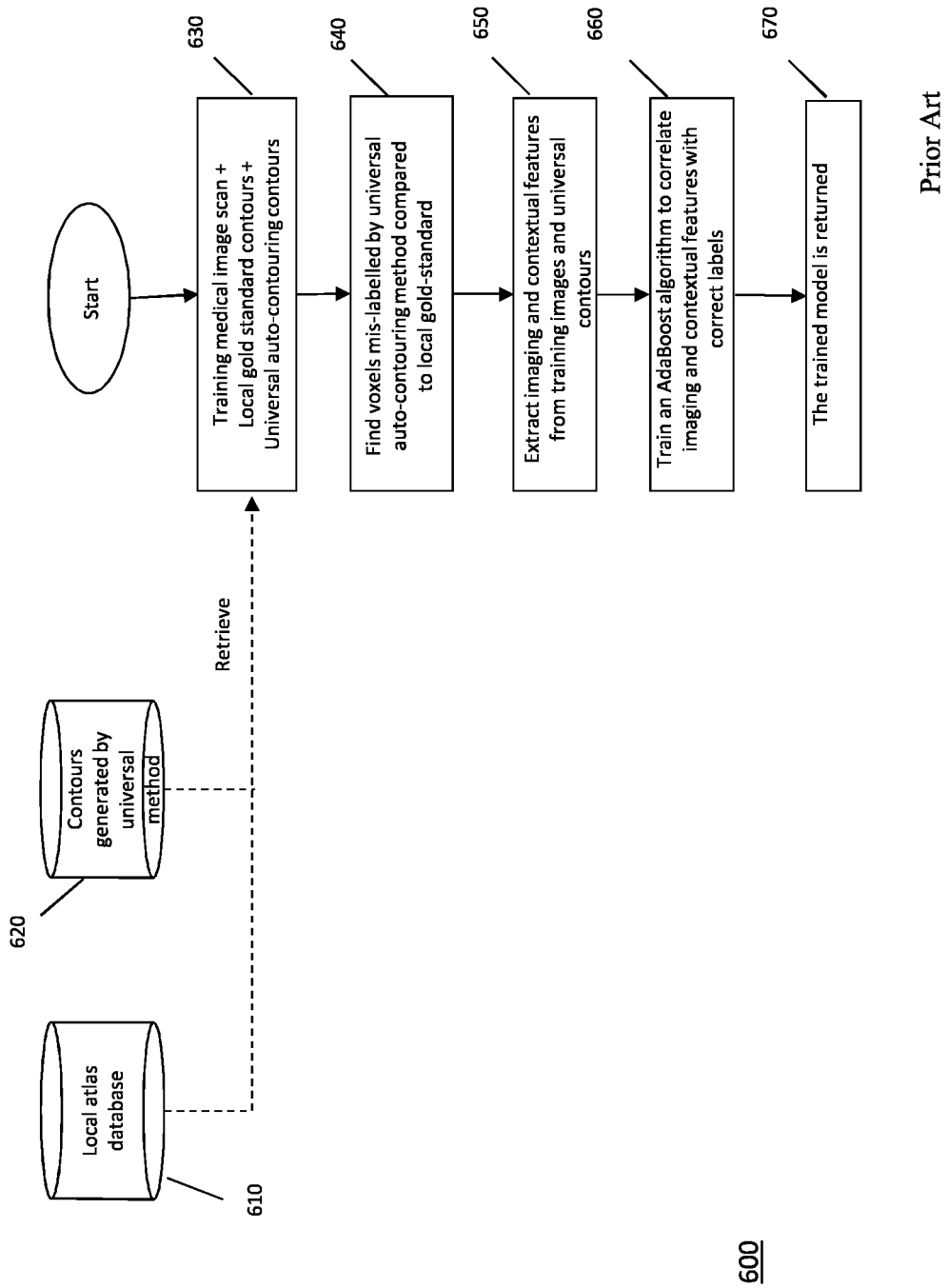
FIG. 6 illustrates an implementation of a known local customisation method shown in FIG. 5.
Figure 7:
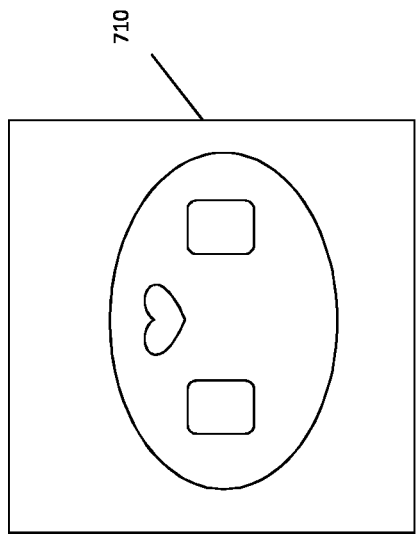
FIG. 7 illustrates the outcome of applying a known local customisation method of auto-contouring to a medical scan image.
Figure 7:
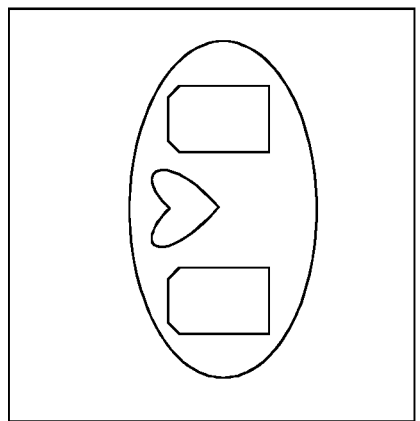
Figure 7:
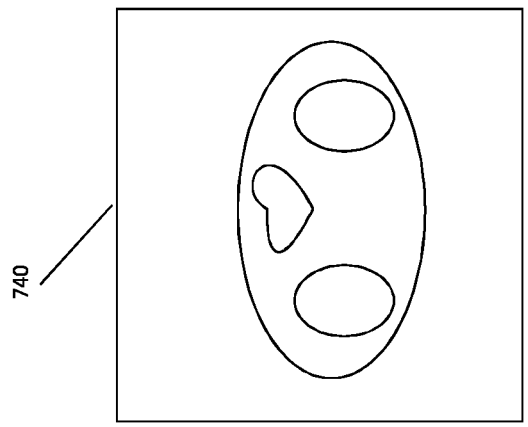
Figure 7:
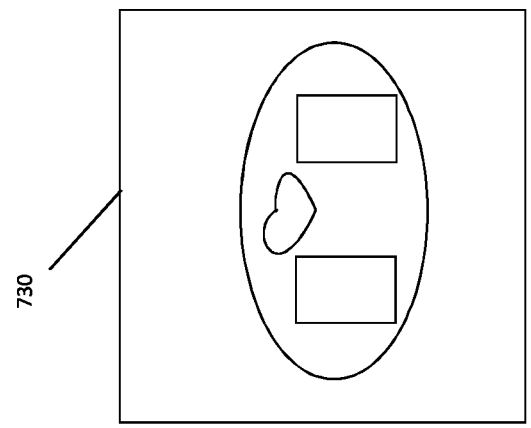
Figure 7:
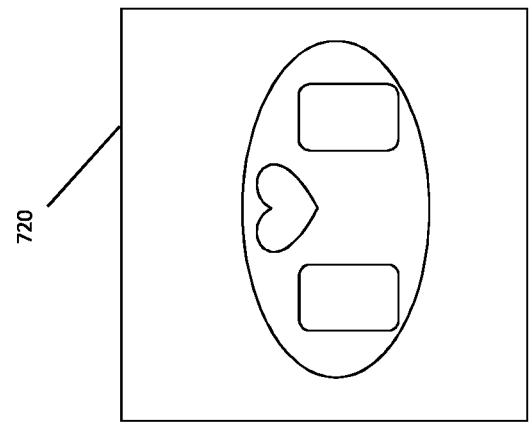

The local auto-contouring customisation operation 940 may use machine learning techniques to learn to adapt the universal contours 930 to the institutional/departmental guidelines. One example of how to implement such an adaptation would be to use the method of Wang, as illustrated in FIG. 6. In this particular implementation, a machine learning classifier learns to detect regions of the image scan which are wrongly classified by the universal auto-contouring method, while a second classifier corrects the outcome of the regions highlighted by the first classifier. Local intensity and appearance features can be used as input to the classifiers.

Local auto-contouring customisation operation 940 learns to cope with both systematic and random variations. Such variations are introduced by intra- and inter-operator variability in contouring, and by discrepancies between institutional/departmental guidelines.

The set of local contours 950 generated by the local auto-contouring step 940 adhere to the local protocol requirements. These local contours 950 are, therefore, more accurate with respect to the local gold-standard contours. The institution that operates those local protocol requirements will therefore typically find the set of local contours 950 more acceptable than the set of universal contours 930.

The generated set of local contours 950 is displayed to the operator for review. As shown as step 960, the displayed local contours 950 may require further editing 960 before approval. This editing may be able to take account of features or peculiarities of the medical scan image 905 that have not been processed optimally in local auto-contouring customisation operation 940, or at some step or steps before this point.

Following any further editing and acceptance 960 of the set of local contours 940, the local contours are available for updating the local atlas database 910. At step 965, the set of local contours 950, after approval 960, and the medical scan image 905 are added to local atlas database 910. Notably, such a step 965 of updating the local database is, for example, not shown in reference [10].

Figure 8:
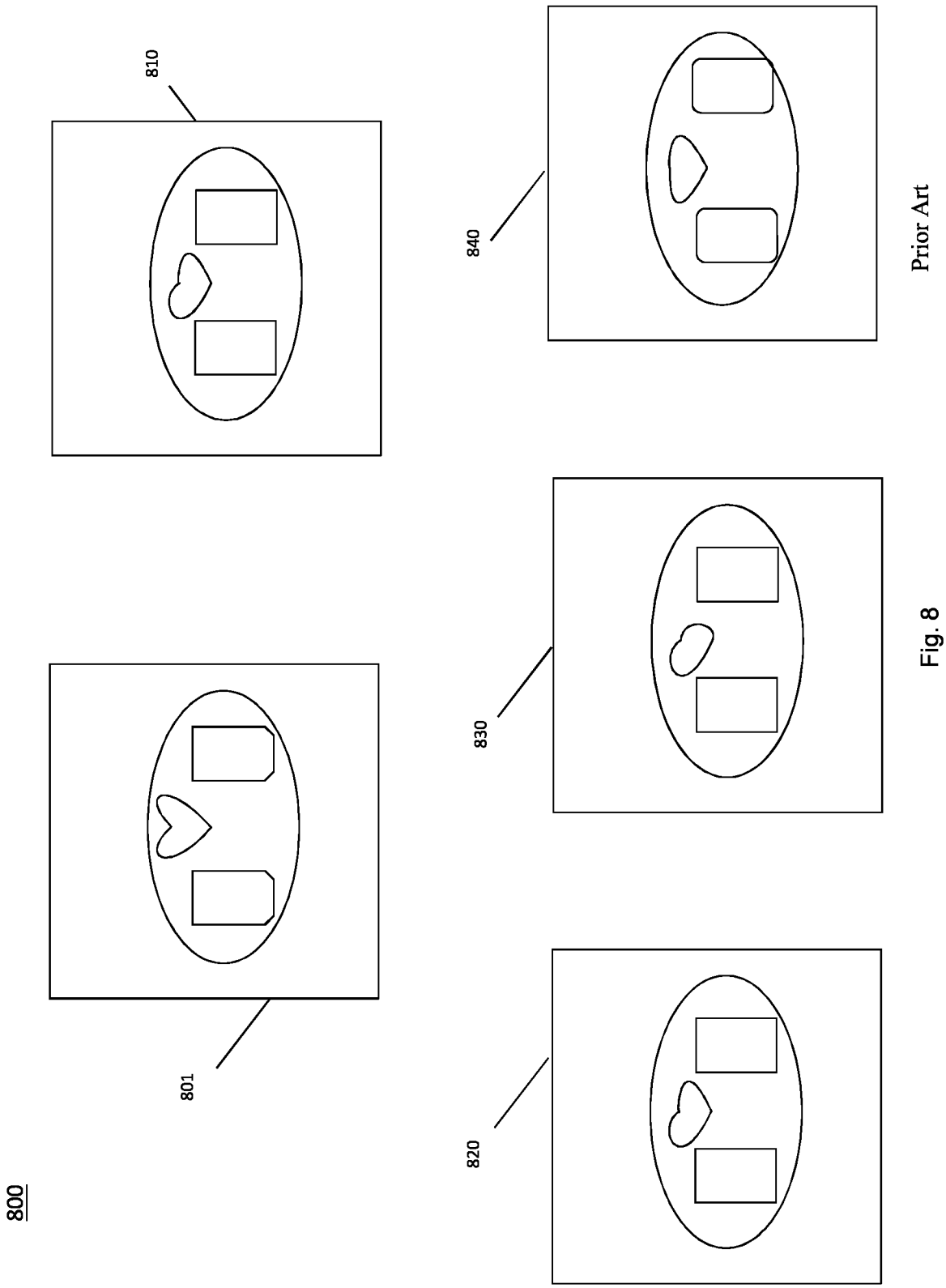
FIG. 8 illustrates the outcome of a known method when a universal atlas database is used to contour new data.

Method 900 of the invention also enables the update of the universal atlas database 901. Method 900 aims to add only approved gold-standard local contours to the universal atlas database 901. In order to achieve this, method 900 provides compensation for the biases introduced by the local auto-contouring step 940. Adding the set of local contours directly to universal atlas database 901 with no prior standardisation would introduce unwanted biases. Those unwanted biases would disrupt subsequent performances of universal auto-contouring operation 920. The biases would also feed through to and disrupt any subsequent local auto-contouring step 940 that uses such universal contours, as illustrated in FIG. 8.

Standardising step 980 of method 900 enables a global standardisation of the generated local contours 950 after editing/approval 960, which thereby provides a set of standardised global contours 985 for the medical scan image

905. Standardising step 980, therefore, ensures compliance with the universal contouring guidelines.

Standardising 980 the set of local contours 950 to provide the set of standardised global contours 985 is done using a trained model. The trained model compensates for biases in the set of local contours 950 after editing/approval 960, thereby creating the set of standardised global contours 985 that is appropriate for the particular medical scan image 905. The model may have been trained using machine learning, and may have been trained to be able to standardise the accepted local contours 960 to ensure conformity to the universal database contouring criteria.

After global standardisation step 980, the set of standardised global contours 985 and the corresponding medical image 905 are added at step 990 to universal atlas database 901. The set of standardised global contours 985 is then available as part of a new atlas in universal atlas database 901. The new atlas in universal atlas database 901 joins the other atlases that were already stored in universal atlas database 901, and may then be used in a subsequent application of operation 920 on another new medical scan image.

In summary, the local contouring customisation operation 940 serves to adapt the set of universal contours 930 to the local institutional/departmental guidelines. Subsequently, the step of standardising 980 the set of approved local contours 960 removes the biases due to the local guidelines, thereby allowing method 900 to create the set of standardised global contours 985 to incorporate as part of the new atlas into the universal atlas database 901. Hence the new atlas is available for subsequent iterations of universal autocontouring operation 920, and so constitutes an expansion of universal atlas database 901 and/or an update to the universal auto-contouring model.

When the set of universal contours 930 is generated at step 920, the universal contours 930 may require editing and cannot be added directly to the universal atlas database 901. When operators assess the quality of the contours before approval at step 960, they only do so according to the local standard. So the set of local contours cannot be added directly to universal atlas database 901. In accordance with the invention, the separate standardising step 980 is applied to the approved local contours 950, after editing and acceptance of the local contours 950 at step 960.

The ability to perform universal auto-contouring operation 920 and local auto-contouring customisation operation 940 with the expanded atlas databases 901, 910 allows both the models used in steps 920 and 940 to improve robustness and accuracy. In particular, the expansion of the universal atlas database 901 using atlases that have undergone the global standardising 985 of the set of local contours ultimately improves the ability of auto-contouring step 920 and local auto-contouring step 940 to describe both variation of the anatomy within the population and the imaging protocol. A single universal atlas database 901 that has been expanded according to method 900 can be utilised for step 920 in any local institution, i.e. in potentially hundreds of local institutions. Thus the method 900 allows auto-contouring to be better adapted to work within a multi-institutional or even a global environment.

Method 900 has so far been described for a single medical scan image 905. However, method 900 may be repeated for a plurality of medical scan images 905, thereby creating a set of standardised global contours 985 for each of those medical scan image 905. A new atlas can then be added to the universal atlas database 901 for each of the plurality of medical scan images 905. Each new atlas comprises the medical scan image 905 and the set of standardised global contours 985 for that medical scan image 905.

Table 1 below shows an illustration of the contents of universal atlas database 901. The left column shows ten atlases. The numerical sequence 1-10 is the order in which the atlases were added to the universal atlas database 901. The right column describes the source/origin of each atlas. In a real universal atlas database 901, there might be hundreds of atlases for one particular organ, such as a liver.

TABLE 1

Illustration of the origin of the contents of a universal atlas database 901

| Atlas number | Source of each atlas |
|---|---|
| 1 | Derived from a medical scan taken for the purpose of starting the universal atlas database 901, with the contours selected and approved by a radiographer. |
| 2 | Derived from a medical scan taken for the purpose of starting the universal atlas database 901, with the contours selected and approved by a radiographer. |
| 3 | Derived from a medical scan taken for the purpose of starting the universal atlas database 901, with the contours selected and approved by a radiographer. |
| 4 | Derived by execution of step 980, on a first set of local contours 960 that result from the execution of steps 905, 920, 930, 940 and 950 on a first medical scan image at a first institution A. |
| 5 | Derived by execution of step 980, on a second set of local contours 960 that result from the execution of steps 905, 920, 930, 940 and 950 on a second medical scan image at a first institution A. |
| 6 | Derived by execution of step 980, on a third set of local contours 960 that result from the execution of steps 905, 920, 930, 940 and 950 on a third medical scan image at a first institution A. |
| 7 | Derived by execution of step 980, on a fourth set of local contours 960 that result from the execution of steps 905, 920, 930, 940 and 950 on a fourth medical scan image at a second institution B. |
| 8 | Derived by execution of step 980, on a fifth set of local contours 960 that result from the execution of steps 905, 920, 930, 940 and 950 on a fifth medical scan image at a second institution B. |
| 9 | Derived by execution of step 980, on a sixth set of local contours 960 that result from the execution of steps 905, 920, 930, 940 and 950 on a sixth medical scan image at a third institution C. |
| 10 | Derived by execution of step 980, on a seventh set of local contours 960 that result from the execution of steps 905, 920, 930, 940 and 950 on a seventh medical scan image at a fourth institution D. |

As shown in table 1, an initial set of three atlases may be added to the universal atlas database 901, based on the work of a radiographer who has approved contours on medical scan images that have deliberately been taken to start off the universal atlas database 901. These atlases 1-3 may have been available from a pre-existing medical study, for example. The atlases 1-3 are then available for use in step 920, when method 900 runs for a new medical scan image taken at one of various institutions, for example as part of a continuation of their research.

The institutions A-D mentioned in rows four to ten of table 1 for atlases 4-10 have each derived a set of approved local contours 960 for each of one or more images that they have taken for this purpose, or that they hold. After global standardising 980 of each set of approved local contours 960, universal atlas database 901 can be expanded with the resulting atlases. First institution A provides atlases 4-6. Second institution B provides atlases 7 and 8. Third institution C provides atlas 9. Fourth institution D provides atlas 10.

As described above, method 900 may result in the newly created atlas(es) being added to the universal atlas database 901. Alternatively, the first atlas may be added to a second local database that is held by the local institution or department. Such a second local database would be held by the local institution in addition to local atlas database 901 shown in FIG. 9, and may be available only to that local institution. The second local database would be a database of atlases created in accordance with the operation of method 900, i.e. those produced at step 980. The atlases in the second local database are in contrast to those in the local atlas database 910, which is a repository of atlases that represent the local gold-standard contours available to each institution/department. The second local database may be employed by an institution that wished to benefit from method 900, but when universal atlas database 901 is either: (i) Not receiving new atlases at step 990; or (ii) is receiving new atlases at step 990, but those new atlases are not being made available to the local institution. In effect, a local institution can create a second local database, and populate it with new atlases created in step 980, without being reliant on the operators of universal atlas database 901 to use method 900. The operators of local atlas database 910 could employ the method 900 themselves. Those operators can thereby build the second local database themselves, for their own use.

The local auto-contouring customisation operation 940 and subsequent steps may comprise further details, as follows. The local auto-contouring customisation operation 940 may comprise adaptation of the universal contours 930 to local guidelines of a local institution. This local institution may be the institution that both provides the medical scan image 905, and holds the local atlas database 910. The local institution may perform both the universal auto-contouring operation 920 and the local auto-contouring customisation operation 940.

Performing the local auto-contouring customisation operation 940 on the medical scan image 905 may be performed with input 912 from the local atlas database 910. The input from the local atlas database 910 to the local auto-contouring customisation operation 940 may comprise a local atlas from the local atlas database 910, or may comprise multiple local atlases from the local atlas database 910.

Step 960 may comprise providing the set of local contours 950 to a user for approval or editing, prior to the step of standardising 980 the set of local contours using the trained model. Furthermore, the set of universal contours 930 may be used in a training step, which is not shown in FIG. 9. The training step comprises comparing the set of universal contours 930 to the set of local contours 950, in order to further optimise an algorithm that performs the standardising 980 of the set of local contours.

Figure 1:
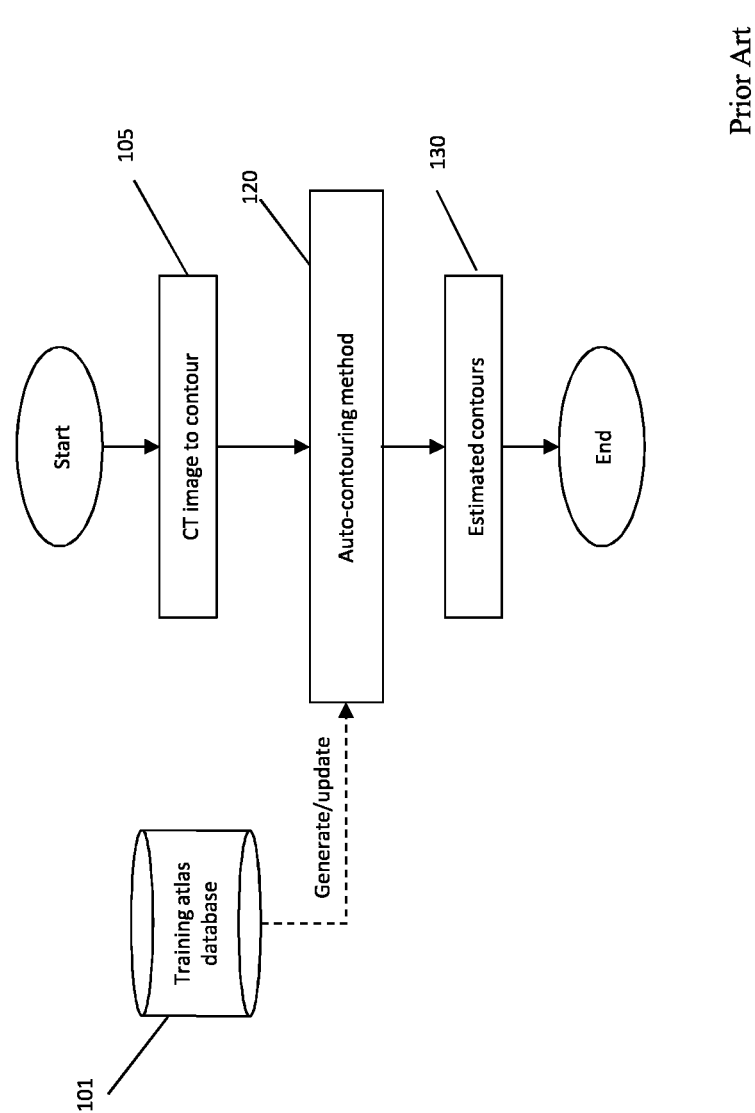
FIG. 1 illustrates a generic auto-contouring method.
Figure 2:
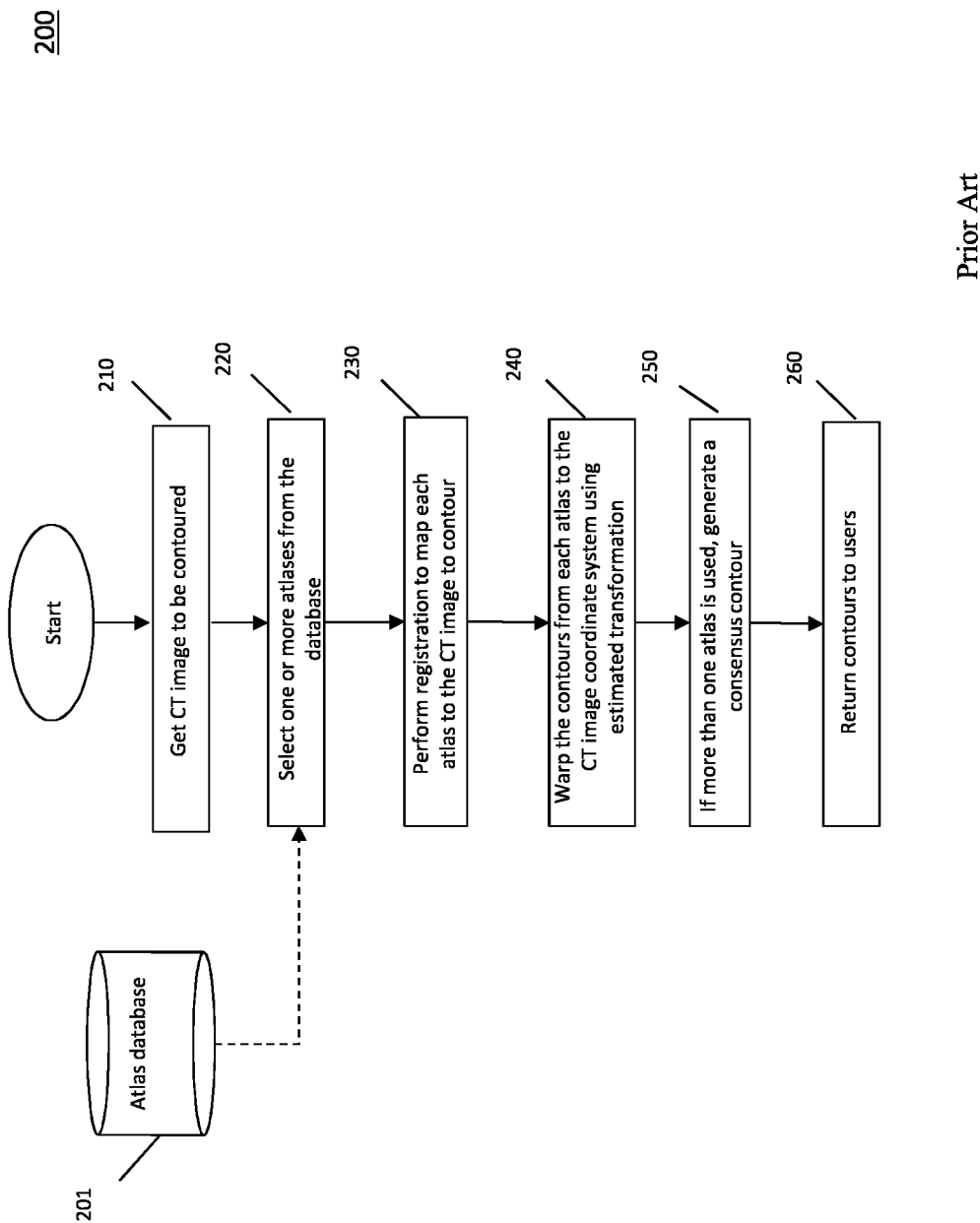
FIG. 2 illustrates a generic atlas-based auto-contouring method.
Figure 3:
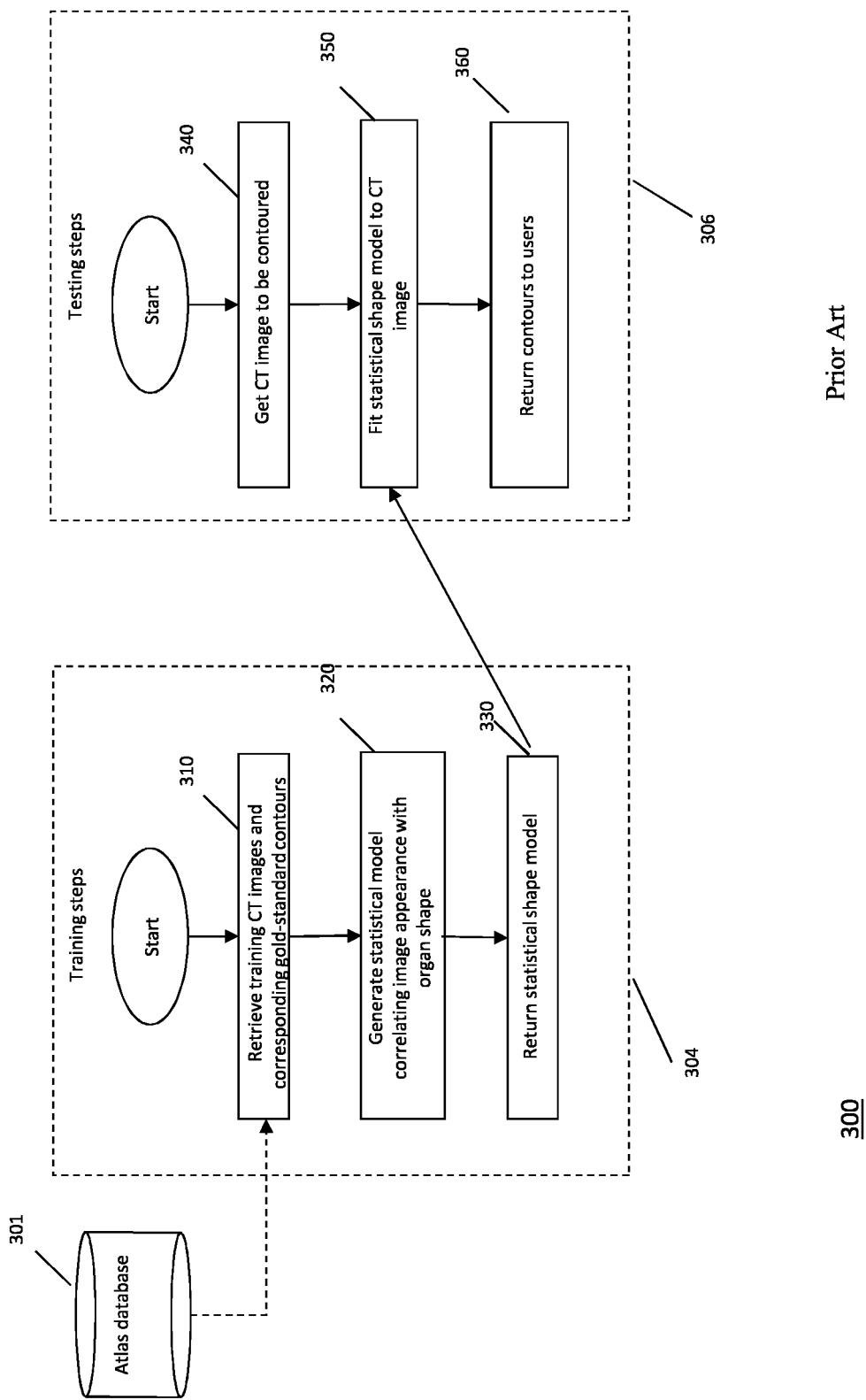
FIG. 3 illustrates a generic statistical shape and appearance auto-contouring method.
Figure 4:
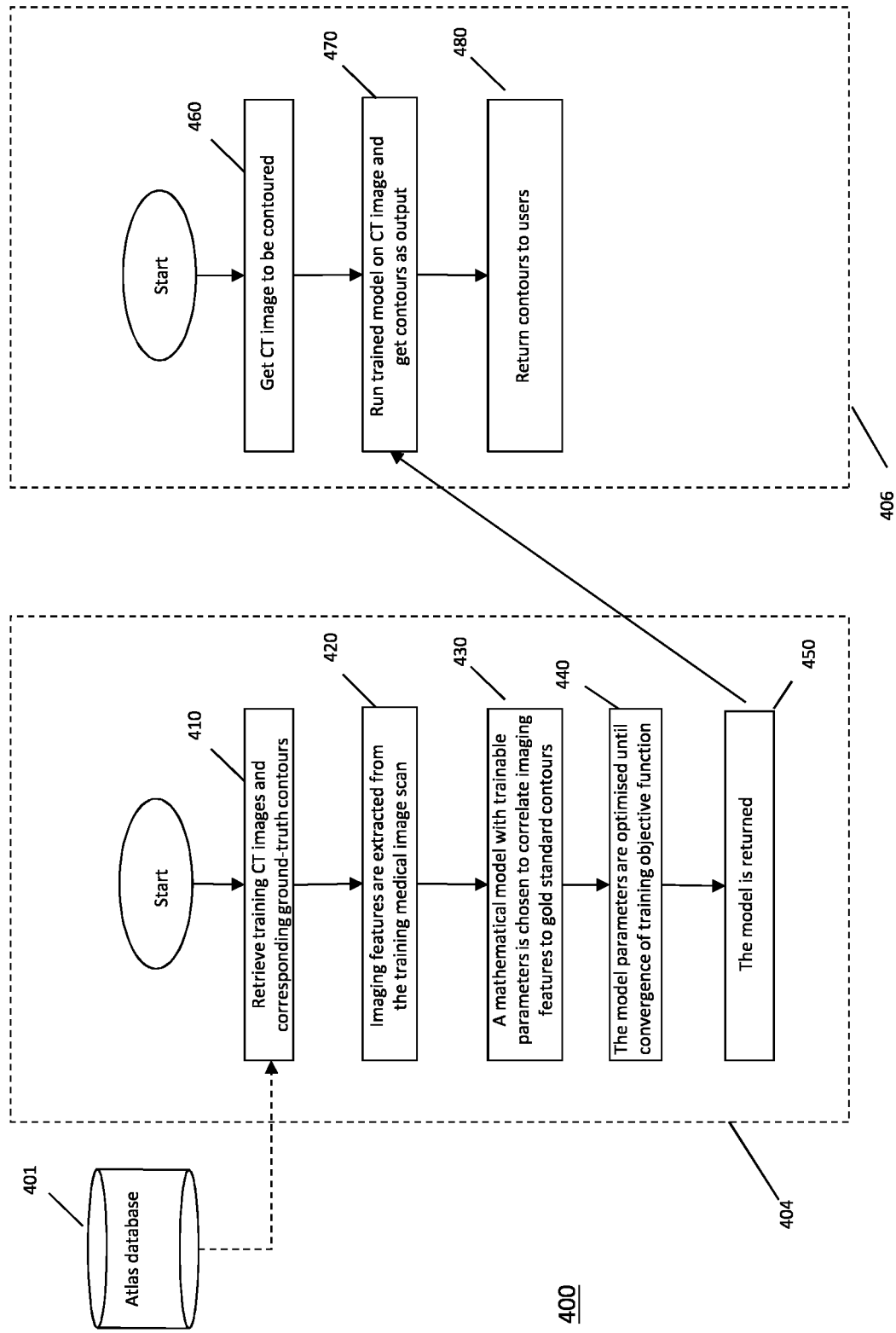
FIG. 4 illustrates a generic machine learning auto-contouring method.
Figure 5:
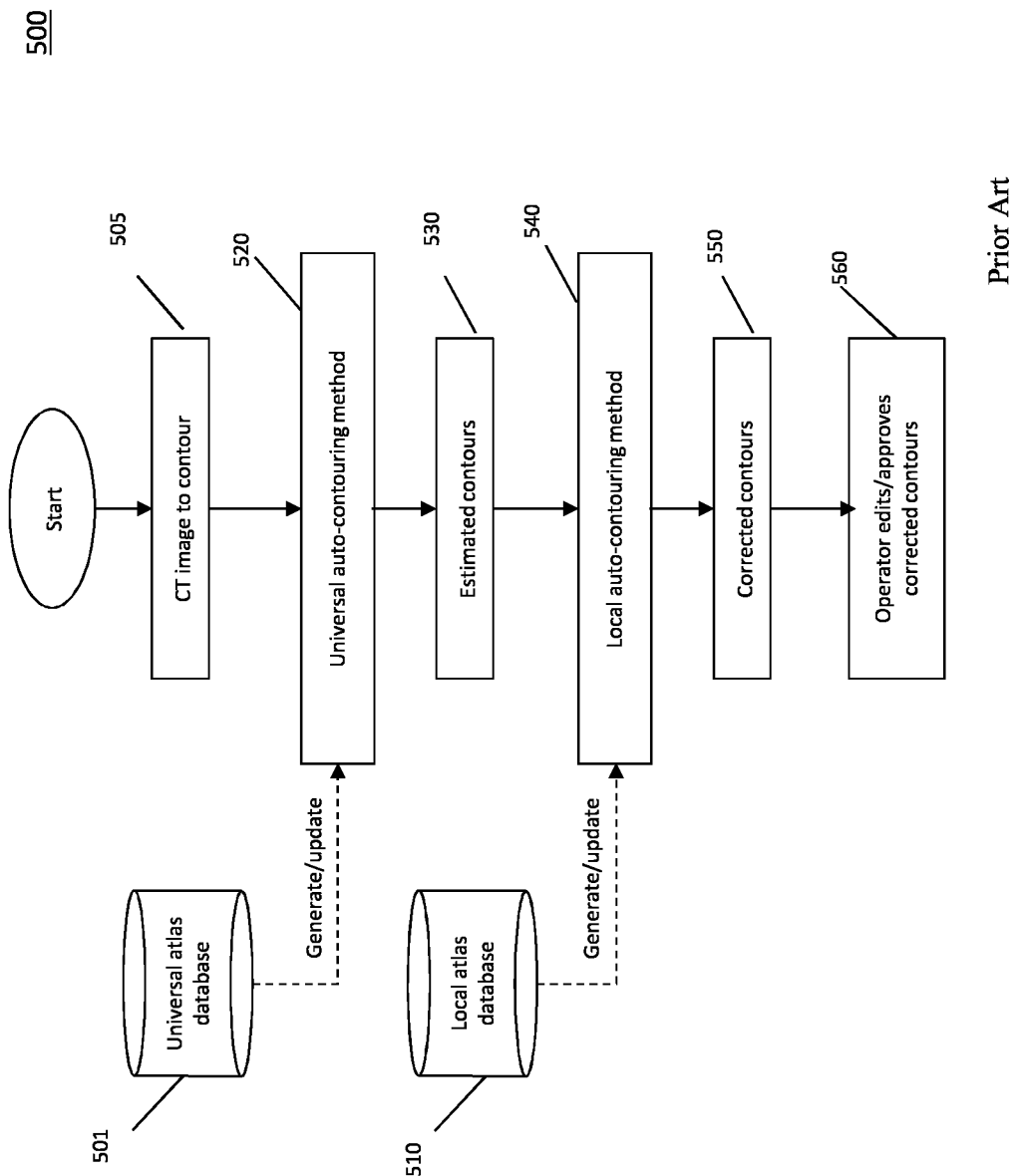
FIG. 5 illustrates a known local customisation method of auto-contouring a medical scan image.

The ability to update both the universal auto-contouring operation 920 and the local auto-contouring customisation operation 940 with newly generated atlases allows the models to improve robustness and accuracy. This is achieved by increasing their ability to better describe both variation of the anatomy within the population, and the imaging protocol. Furthermore, auto-contouring can be better adapted to work within a multi-institutional environment than was the case with known systems. Method 900 could also be either atlas-based or model-based as well, i.e. the new standardised atlases created in method 900 and included in the universal atlas database 901 can be used to improve the universal contouring operation 920 regardless of whether it is implemented with an atlas-based technique (FIG. 2) or a model-based technique (FIG. 3).

FIG. 10

Figure 10:
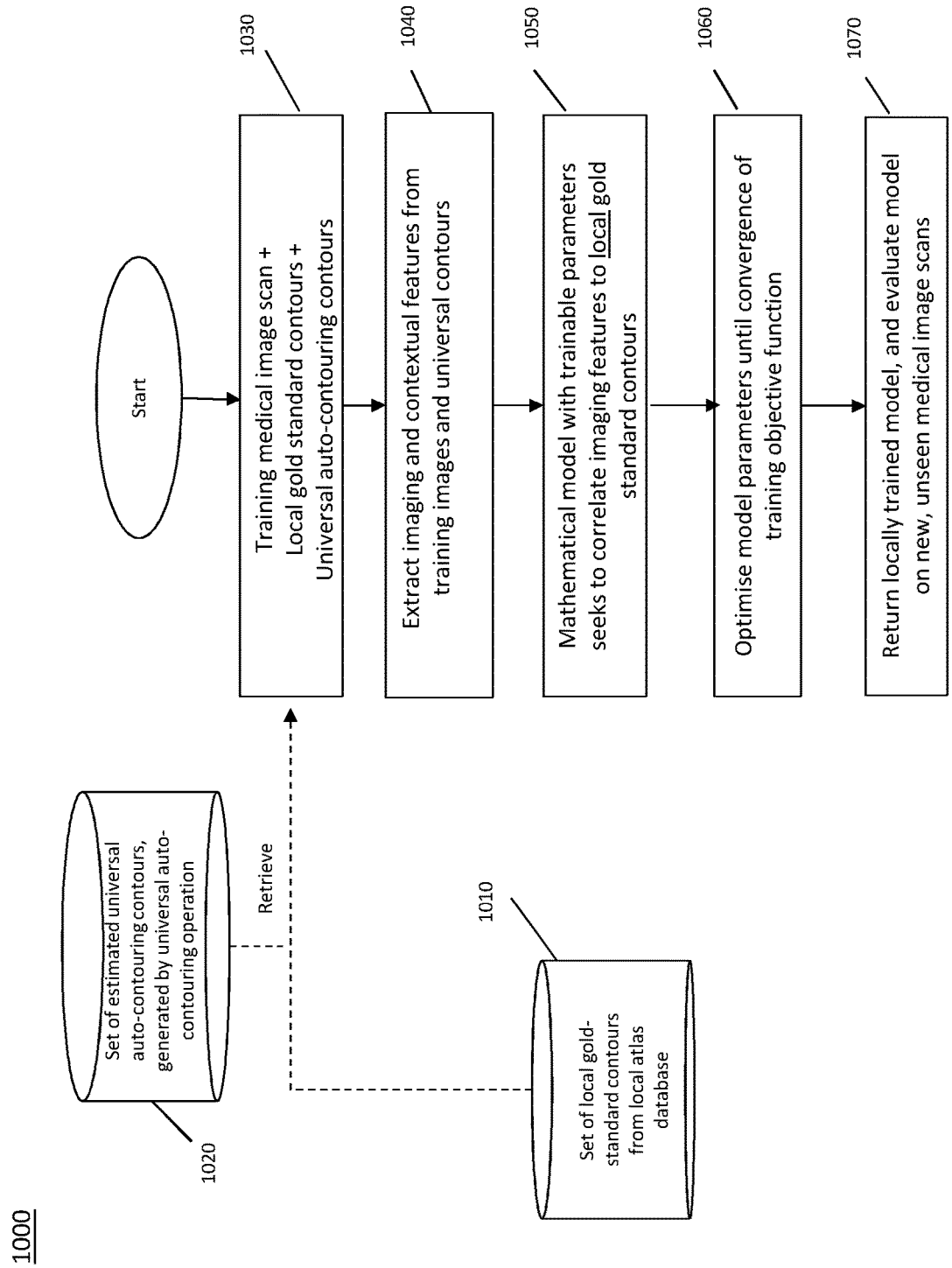
FIG. 10 illustrates an implementation of a training method for the local contouring customisation operation.

FIG. 10 illustrates an implementation of a training method for the local contouring customisation operation. The local contouring customisation operation is based on a model, which the method of FIG. 10 trains, prior to use of the model. In the example of FIG. 10, the model is a machine learning model. The local contouring customisation operation is the operation that is applied, after completion of training, in the local customisation operation 940 of the embodiment of FIG. 9.

The training method 1000, shown in FIG. 10, for the local customisation operation seeks to predict a local 'gold-standard' contour, starting from the inputs 1030 of: (i) the training medical image scan; (ii) a set of estimated universal auto-contouring contours 1020 for the training medical image scan; and (iii) a set of local gold-standard contours 1010 for the training medical image scan. The set of local gold-standard contours originates from local atlas database 1010. The set of estimated universal auto-contouring contours 1020 originates from performance of the universal auto-contouring operation 920 on the training medical image scan.

In order to train the model that is to be used by the local customisation operation 940, the training medical image scan, the set of local gold-standard contours 1010 and the estimated universal auto-contouring contours 1020 need to be available for a number of cases.

During training of the machine learning model, image features, derived from intensities, gradients, and local context, are extracted 1040 from the training medical image scan and from the estimated universal auto-contouring contours 1020. These extracted features seek to characterise an underlying pattern in the data, namely the relationship between scan image appearance and contours.

A machine learning algorithm 1050 is then applied to the extracted features, and is used to estimate local contours from the extracted features. The machine learning algorithm comprises a mathematical model with trainable parameters, which seeks to correlate imaging features to the set of local gold-standard contours 1010. This is because the feature extraction is to be optimised as part of the training process. Examples of the machine learning algorithm 1050 are support vector machines, decision trees or neural networks, which can be used to estimate the local contours from the extracted features. In deep learning algorithms, such as convolutional neural networks, the features are not specified in advance.

During application of the training method 1000, the internal parameters of the algorithm are optimised 1060 based on each performance of the correlation step 1050. The optimisation 1060 is such that the estimated local contours, i.e. the model-predicted local contours, match the set of gold-standard local contours 1010, as closely as possible. The extent to which they match is quantified by a cost function, which could be, for instance, the difference in the predicted and gold-standard contours. The cost function may also be described as a 'loss' or 'objective' function. During training, the optimisation 1060 automatically seeks to derive or shape a model with parameters that minimise the cost function.

When optimisation step 1060 is complete, the training stage is finished and the trained machine learning model is returned 1070. The trained machine learning model is then used 1070 for predicting the local contours for new medical image scans, for which universal contours have been generated, i.e. in the local contouring customisation operation 940 of FIG. 9.

FIG. 11

Figure 11:
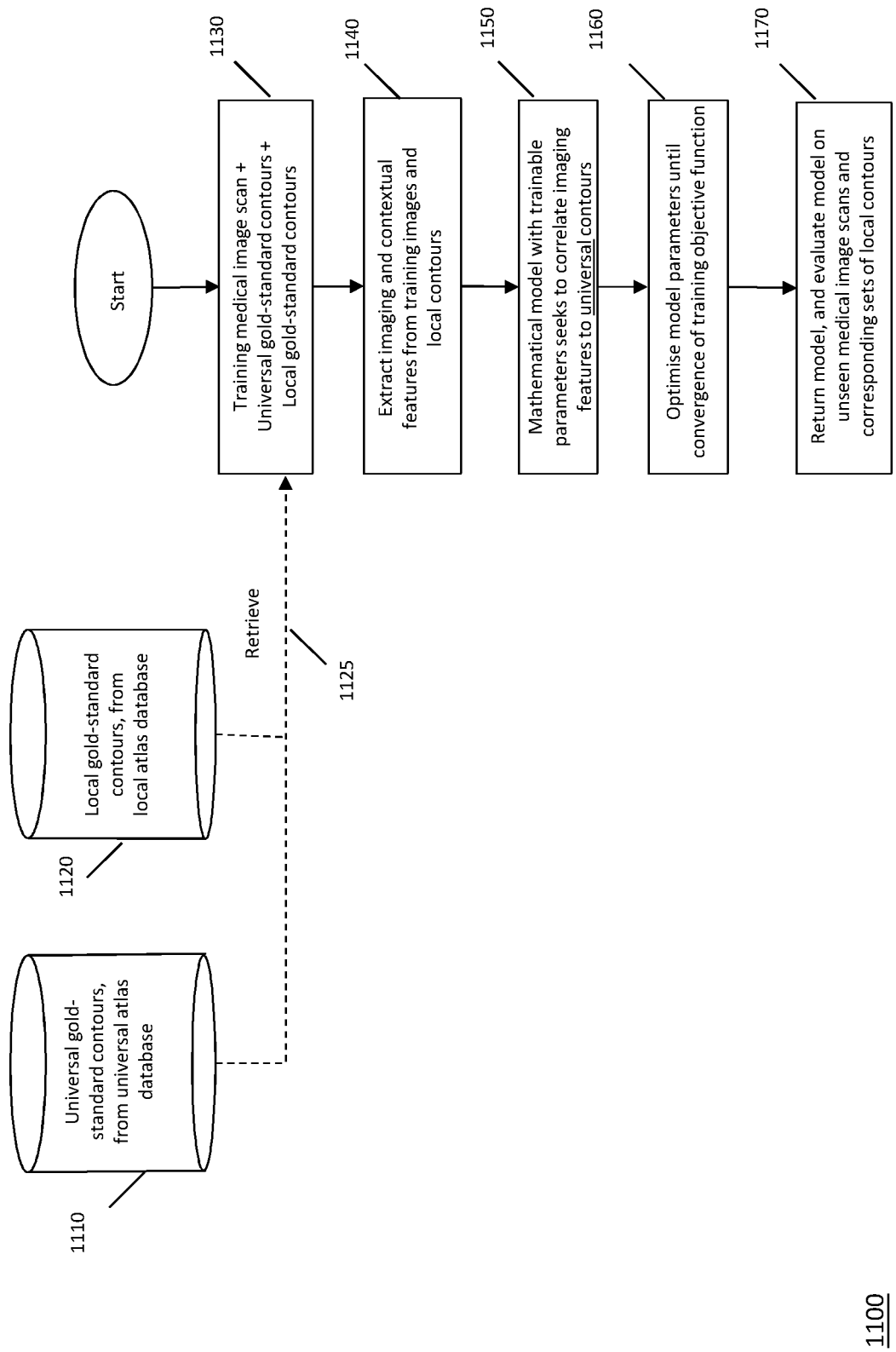
FIG. 11 illustrates details of a training method for the universal standardisation operation.

FIG. 11 illustrates details of a training method for the universal standardisation operation that is applied to the set of local contours. The universal standardisation operation is the operation that is applied, after training, in global standardisation step 980 of the embodiment of FIG. 9. The standardising of the set of local contours in step 980 seeks to compensate for local effects introduced in steps 940 and 960, and thus to prepare data for use by a wider range, i.e. a global range, of institutions. The result of step 980 is the creation of a set of global contours to add to the universal atlas database 901, in step 990, together with the medical scan image.

The training method 1100, shown in FIG. 11, to derive the standardising operation 980, seeks to predict a universal gold-standard contour. The starting inputs 1130 are: (i) a training medical image scan; (ii) global gold-standard contours 1110 for the training medical image scan; and (iii) a set of approved, gold-standard local contours 1120 for the training medical image scan. The set of approved local contours 1120 originates from step 960 of FIG. 9. For training purposes, the training medical image scan, the global gold-standard contours 1110 and the set of approved local contours 1120 need to be available for a number of cases.

During training of the machine learning model, features derived from intensities, intensity gradients, and local context are extracted 1140 from the training medical image scan and from the set of approved local contours 1120. These extracted features seek to characterise the underlying pattern in the data, namely the relationship between the image appearance and the contours.

A machine learning algorithm 1150 is then applied to the extracted features, and is used to estimate universal contours from the extracted features. The machine learning algorithm comprises a mathematical model with trainable parameters, which seeks to correlate imaging features to the set of universal gold-standard contours 1110. This is because the feature extraction is to be optimised as part of the training process. During the training, the internal parameters of the algorithm are optimised such that the predicted universal contours match the universal gold-standard contours 1110 as closely as possible.

Examples of the machine learning algorithm 1150 are support vector machines, decision trees or neural networks. The machine learning algorithm 1150 is used to estimate the universal contours from the extracted features. In deep learning algorithms, such as convolutional neural networks, the features are not specified in advance.

During application of the training method 1100, the internal parameters of the algorithm are optimised 1160. The optimisation 1160 is such that the estimated universal contours, i.e. the model-predicted universal contours, match the set of universal gold-standard local contours 1110, as closely as possible. The extent to which they match is again quantified by a cost function, which could be, for instance, the difference in the predicted and universal gold-standard contours. The cost function may also be described as a 'loss' or 'objective' function. During training, the optimisation 1160 automatically seeks to derive or shape a model with parameters that minimise the cost function.

When optimisation step 1060 is complete, the training stage is finished. The trained machine learning model is then returned 1170.

The trained machine learning model is used 1170 in routine operation of method 900 for predicting the universal contours that are suitable for inclusion in the universal atlas database 901, at step 990, for new medical image scan images. The prediction will be carried out on a new medical scan image 905, for which a set of approved local contours has already been generated in the local contouring customisation operation 940 and approval step 960 of FIG. 9.

FIG. 12

Figure 12:
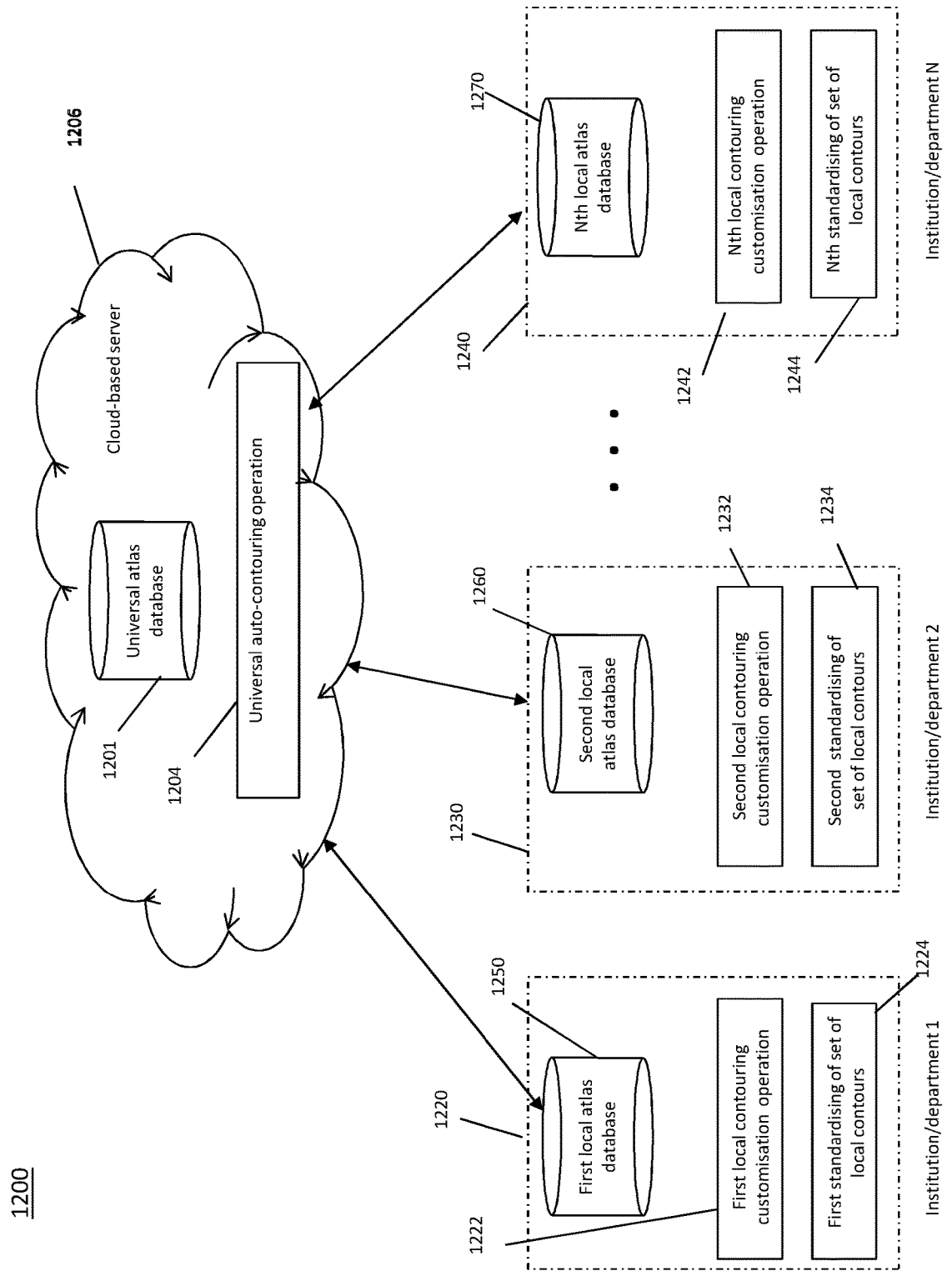
FIG. 12 illustrates a cloud-based embodiment of the invention.

FIG. 12 illustrates a cloud-based embodiment of the invention. In the embodiment 1200 of a configuration of the system, universal atlas database 1201 and universal auto-contouring operation model 1204 may be stored on a cloud-based server 1206.

Cloud-based server 1206 can be accessed by multiple institutions. Each institution may have exclusive access to the local atlas databases and local customisation and standardisation models. First institution 1220, second institution 1230, and 'Nth' institution 1240, are shown in FIG. 12.

Each institution may have exclusive access to a local atlas database, and to local customisation and standardisation models. So a first local atlas database 1250 is in communication with cloud-based server 1206. Similarly, a second local atlas database 1260, and the Nth local atlas database N 1270, are also in communication with cloud-based server 1206.

Each of first 1250, second 1260 and third 1270 local atlas databases can hold local atlases that are appropriate to their local department or institution. However, using steps 980 and 990 of FIG. 9, each of local atlas databases 1250, 1260 and 1270 can supply 990 standardised contours and the corresponding medical image scans, back to universal atlas database 1201. Thus various local departments or institutions can use universal atlases from universal atlas database 1201, but can also contribute to expansion of the pool of universal atlases within universal atlas database 1201.

Each of first institution 1220, second institution 1230, and 'Nth' institution 1240 may therefore be equipped to carry out method 900 of FIG. 9. First local contouring customisation operation 1222 and first standardising of a set of local contours 1224 are carried out by first institution 1220. First local contouring customisation operation 1222 corresponds to step 940 of FIG. 9, but carried out in first institution 1220 to the standards required by the local contouring guidelines that are currently in force in first institution 1220. If first institution 1220 implements a step corresponding to step 965 in FIG. 9, then the first institution 1220 can expand the list of available local atlases in first local atlas database 1250, using local atlases based on the set of local contours and corresponding medical scan image provided by each run of first local contouring customisation operation 1222 on a medical scan image. The first standardising of a set of local contours 1224 is the step that provides the set of standardised global contours that will be supplied 905 with the corresponding medical scan image, back to universal atlas database 1201 from first institution 1220.

Analogously to first local contouring customisation operation 1222 and first standardising of set of local contours 1224, second institution 1230 may comprise second local contouring customisation operation 1232 and second standardising of a set of local contours 1234. Second local contouring customisation operation 1232 will include different steps than those in first local contouring customisation operation 1222, because the local contouring guidelines that are currently in force in second institution 1230 will differ from those in force in first institution 1220. In addition, the application of training method 1000 in second institution 1230 will have provided a second local contouring customisation operation 1232 that has at least some differences in its parameters than the parameters of first local contouring customisation operation 1222.

Nth institution 1240 may comprise Nth local contouring customisation operation 1242 and Nth standardising of a set of local contours 1244.

FIG. 13

Figure 13:
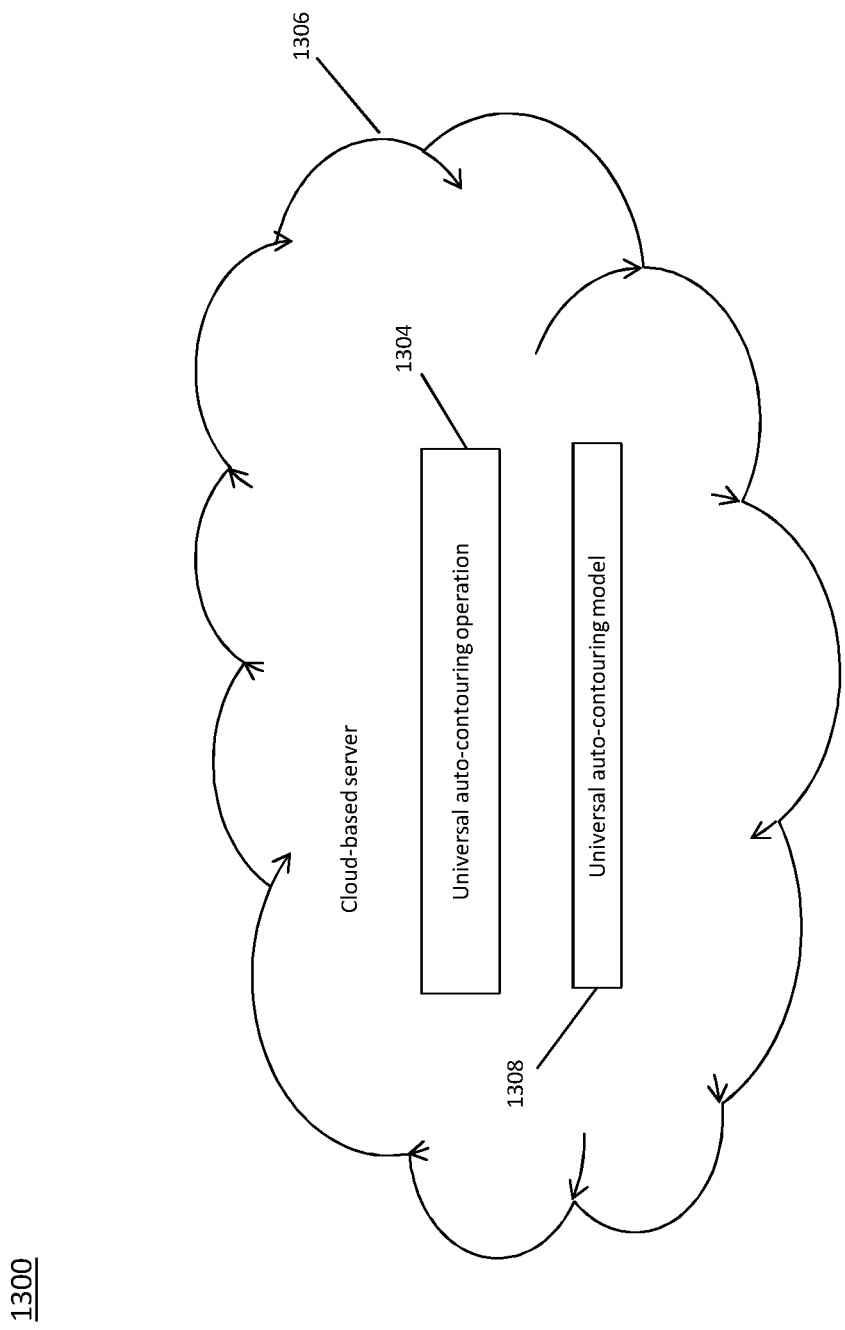
FIG. 13 illustrates a further cloud-based embodiment of the invention.

FIG. 13 illustrates a further cloud-based embodiment of the invention.

FIG. 13 illustrates a variation of the cloud-based portions of the embodiment 1200 of the system shown in FIG. 12. In the embodiment 1300, the cloud-based server 1306 differs from the cloud-based server 1206 of the embodiment 1200.

A universal auto-contouring model 1308 and universal auto-contouring operation 1304 are stored on the cloud-based server 1306.

FIG. 14

Figure 14:
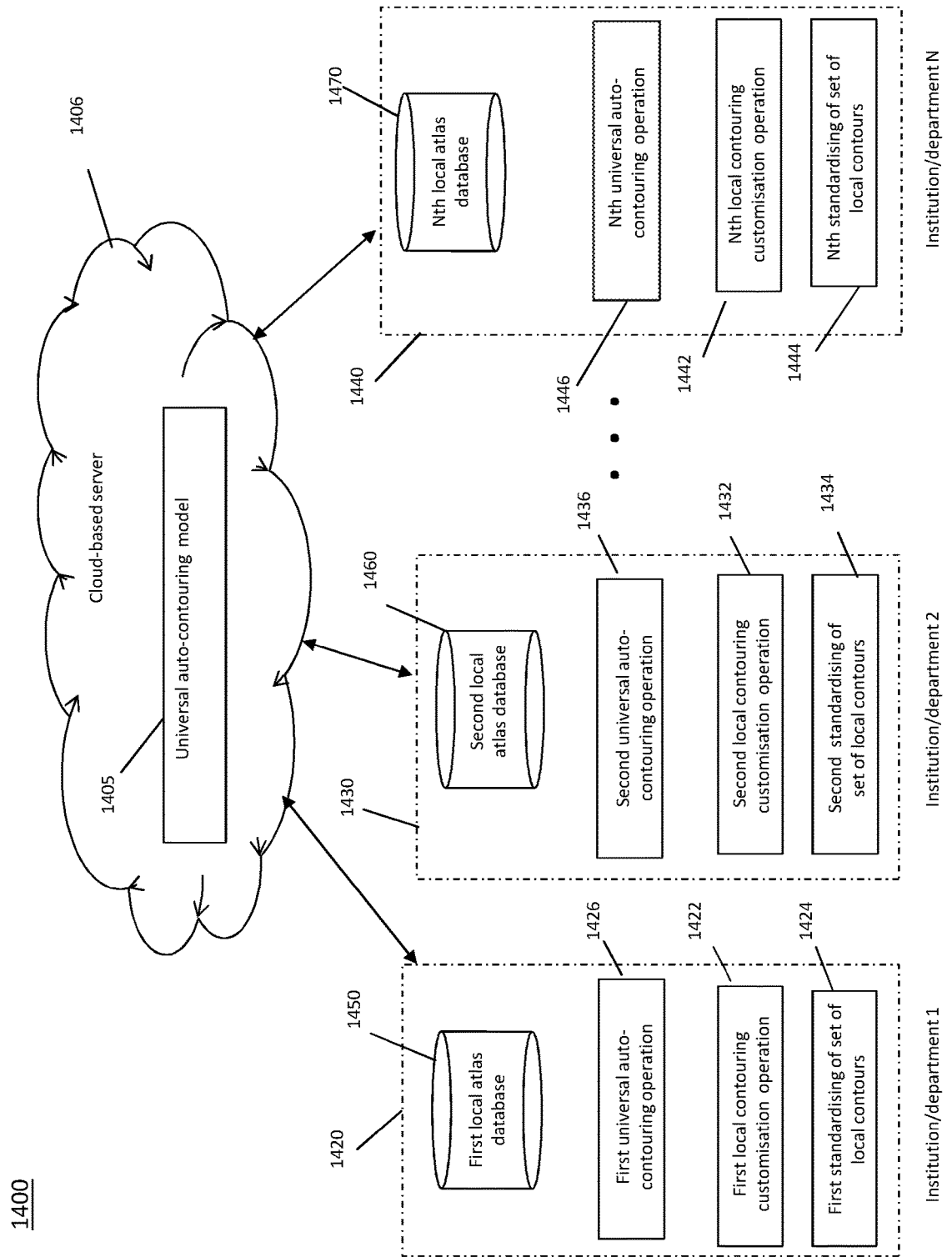
FIG. 14 illustrates a further cloud-based embodiment of the invention.

FIG. 14 illustrates a further cloud-based embodiment of the invention. FIG. 14 illustrates a variation of the embodiment 1200 of the system shown in FIG. 12.

In the embodiment 1400, universal auto-contouring operation model 1405 may be stored on a cloud-based server 1406. A first universal atlas database 1450 is provided in first institution 1420. Otherwise, first institution 1420 comprises first local contouring customisation operation 1422 and first standardising of set of local contours 1424, which function similarly to the corresponding elements in FIG. 12. Analogously, second institution 1430 comprises second local contouring customisation operation 1432 and second standardising of set of local contours 1434. Nth institution 1440 comprises Nth local contouring customisation operation 1442 and Nth standardising of set of local contours 1444.

So a first local atlas database 1450 is in communication with cloud-based server 1406. Similarly, second local atlas database 1460, and the Nth local atlas database N 1470 are also in communication with cloud-based server 1406.

Each of first institution 1420, second institution 1430, and 'Nth' institution 1440 may be equipped to carry out method 900 of FIG. 9. In contrast to the embodiment 1200 of FIG. 12, each of first institution 1420, second institution 1430, and 'Nth' institution 1440 has its own version of the universal auto-contouring operation. First institution 1420 has first universal auto-contouring operation 1426. Second institution 1430 has second universal auto-contouring operation 1436. Nth institution 1440 has Nth universal auto-contouring operation 1446.

Considering for example first institution 1420, first universal auto-contouring operation 1426 may be updated with medical scan images and a corresponding set of global contours that have been generated in a step corresponding to step 980 in FIG. 9, which has been performed in first institution 1420. Over time, the first 1426, second 1436 and third universal auto-contouring operations 1440 will diverge, as various different updates are made to each.

FIG. 15

Figure 15:
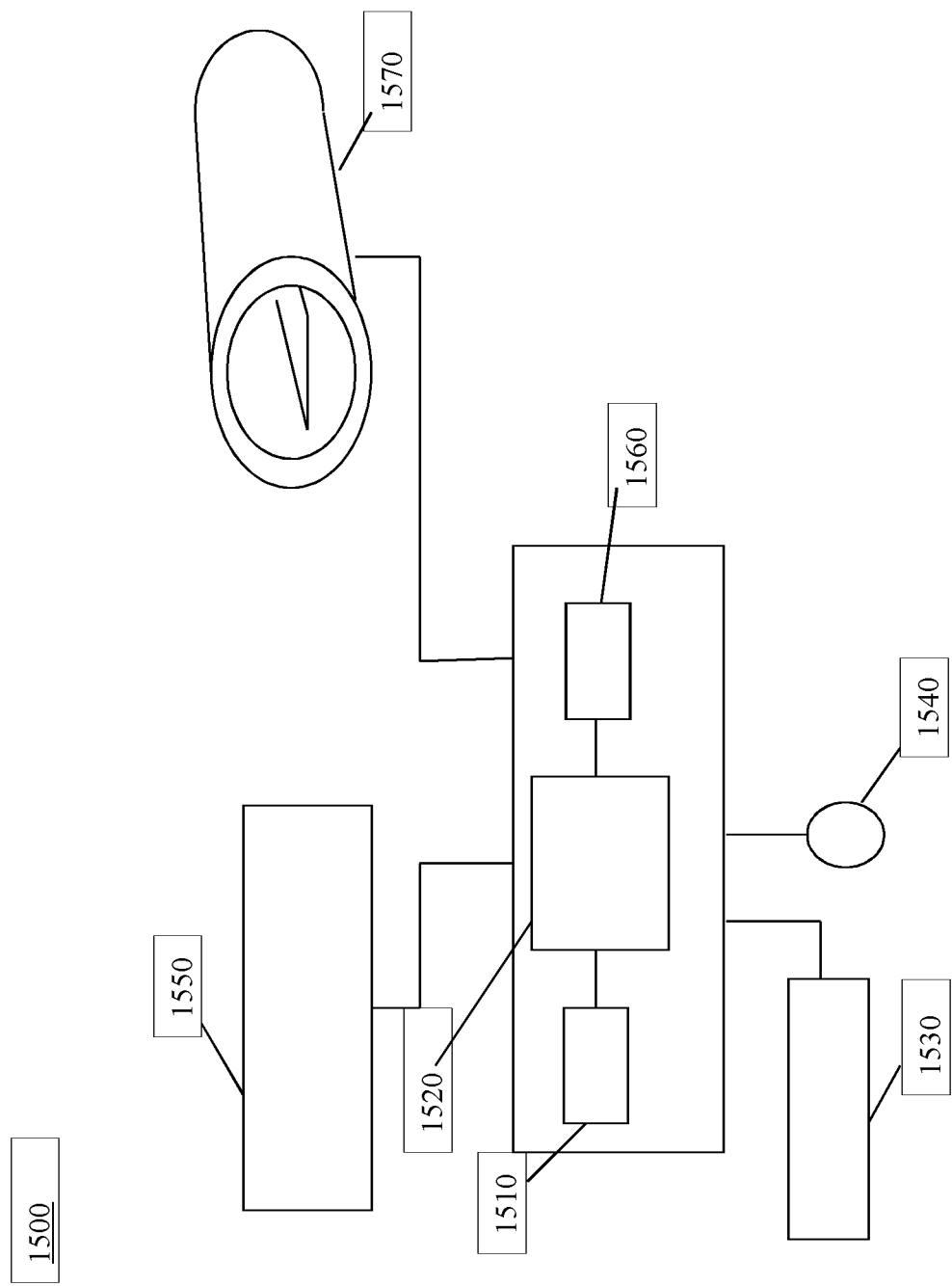
FIG. 15 illustrates a workstation implementation of the invention.

FIG. 15 illustrates a workstation 1500 that implements the invention. FIG. 15 shows a hybrid scanner 1500 in accordance with the invention. Hybrid scanner 1500 comprises keyboard 1530, mouse 1540 and display screen 1550, which facilitate communication with a user of the hybrid scanner 1500.

Hybrid scanner 1500 also comprises a control module 1560 that controls a scanning unit 1570, to provide scan datasets. These may be images of tissue, of a subject inside scanning unit 1570. Medical image scan datasets are produced using different scanning modes. Multi-volume datasets using the same scanning mode can also be provided.

Control module 1560 is linked to memory 1510. Memory 1510 is configured to store a medical scan image 905.

Hybrid scanner 1500 also comprises a processor 1520. Processor 1520 is configured to:

(i) Allow a user to capture and store a medical scan dataset, which provides a medical scan image. The medical scan dataset is stored in memory 1510. The captured medical scan dataset may correspond to the medical scan image 905 in FIG. 9, which is to be contoured. The medical scan dataset may be obtained by scanning a 3-dimensional (3-D) object with one of several scanning modalities.

(ii) Perform a universal auto-contouring operation 920 on the medical scan image 905, with input from the universal atlas database 901, thereby generating a set of universal contours 930 for the medical scan image 905;

(iii) Perform a local auto-contouring customisation operation 940 on the medical scan image 905, with input from a local atlas database 910, thereby generating a set of local contours 950 for the medical scan image 905;

(iv) Standardise 980 the set of local contours 950, using a trained model to compensate for biases in the set of local contours 950, thereby creating a set of standardised global contours 985 for the medical scan image 905.

Display screen 1550 displays some or all of the medical scan images and contour sets. Processor 1520 may perform steps 920 and 940 of FIG. 9. In this case, display screen 1550 may, for example, display an image with universal contours 930 of FIG. 9 and an image with local contours 950 of FIG. 9.

Keyboard 1530, mouse 1540 and screen 1550 allow a user to make edits and indicate approval 960 of the local contours shown at step 960 in FIG. 9.

Analysis module 1520 may also implement each of steps 965, 980 and 985 of FIG. 9. Each of steps 965, 980 and 985 of FIG. 9 may be implemented under the control of the user via interaction with keyboard 1530, mouse 1540 and screen 1550.

FIG. 16

Figure 16:
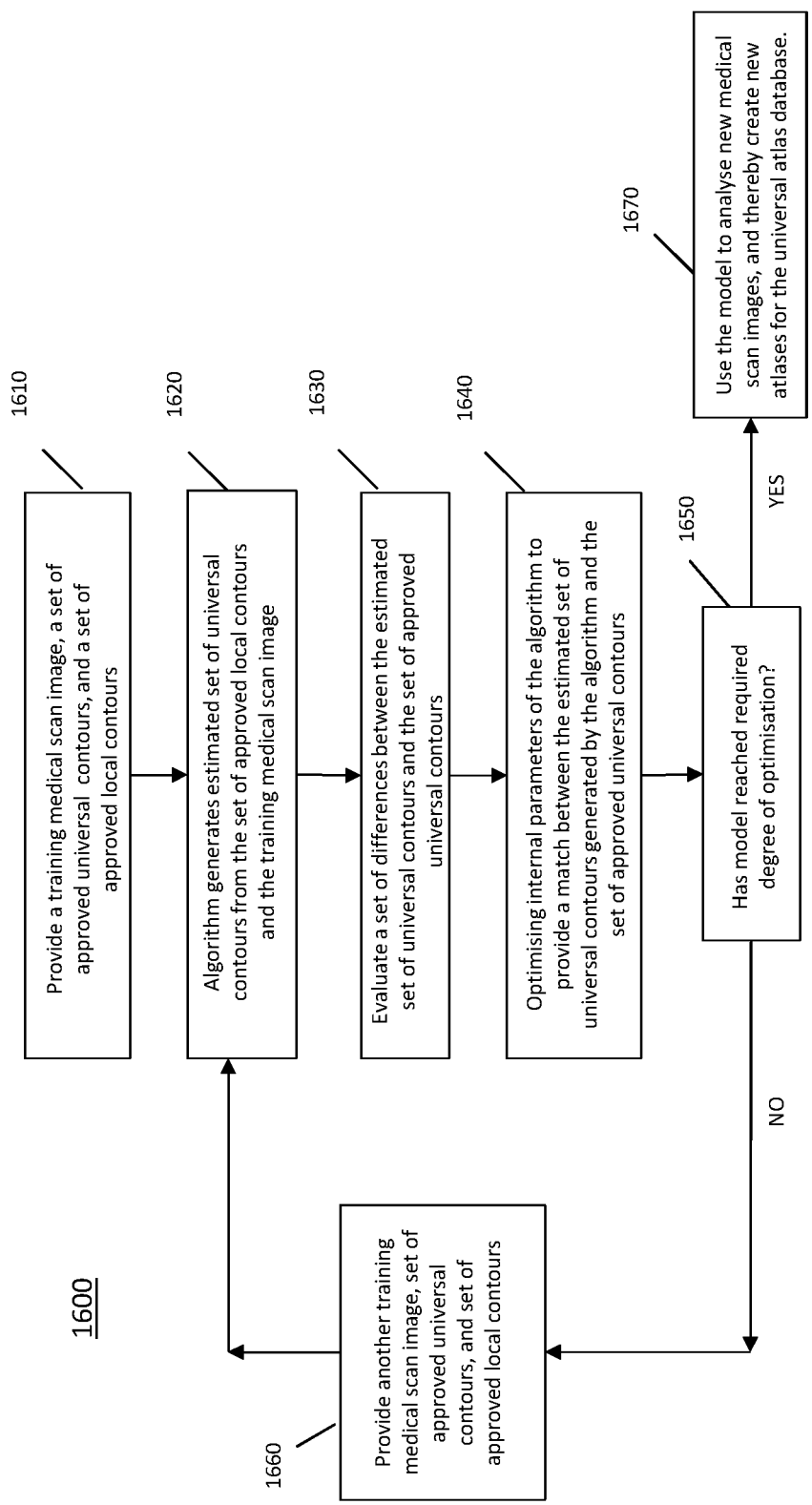
FIG. 16 illustrates an embodiment of a method of training a local contour standardisation model.

FIG. 16 provides an embodiment of a method of training a local contour standardisation model, i.e. the model that will implement the 'standardising of the set of local contours' in step 980 of FIG. 980. FIG. 11 had already provided a general illustration of a method of training a local contour standardisation model. However, FIG. 16 provides details of the embodiment of the training method that is claimed in appended independent claim 16.

Method 1600 comprises an initial step of providing a training medical scan image 905 to the model, a set of approved local contours for the training medical scan image 905, and providing a set of globally approved universal contours for the training medical scan image 905.

Method 1600 then generates 1620 an estimated set of universal contours, from the set of approved local contours and the training medical scan image 905. An algorithm is used to generate 1620 the estimated set of universal contours. The algorithm used in step 1620 may comprise a machine-learning or deep-learning algorithm estimating universal contours from the extracted features, to provide the estimated set of universal contours.

A set of differences is evaluated 1630 between the estimated set of universal contours and the set of globally approved universal contours. Based on these differences, the internal parameters of the model are optimised 1640 to provide a match between the estimated set of universal contours generated by the algorithm and the set of approved universal contours.

A decision 1650 is made whether the model has reached the required degree of optimisation. If the answer is 'NO', then another training medical scan image, another set of approved universal contours, and another set of approved local contours will be provided 1660. The method 1600 then returns to step 1620. Steps 1620 to 1650 will then be repeated for as many other medical scan images 905 and their sets of approved local contours and globally approved universal contours as necessary, until the evaluated 1630 set of differences is smaller than a given threshold.

When the answer at decision box 1650 is 'YES', then the model can subsequently be used 1670 to analyse new medical scan images as explained in connection with method 900 of FIG. 9. Such use of the model thereby creates new atlases for the universal atlas database 901 of FIG. 9.

Steps 1620 to 1660 above have been described in terms of the training medical scan images and their contours going through steps 1620-1640 one at a time, with a decision for each training medical scan image on whether the method has reached an optimal state. However, method 1600 does not have to work in this way. In an alternative sequence, the training medical scan images and their contours can be passed through in batches. When the training medical scan images and their contours are passed through in batches, the extent to which the model has been optimised can still be measured with a loss function. The loss function measures the extent of agreement/disagreement between the estimated universal contours and the approved universal contours. The loss function can be chosen from a variety of possible loss functions. Examples of loss functions can be obtained from measures such as the average Hausdorff distance between contours or the Dice overlap between contours. Loss functions can also be derived from multiple such measures.

Step 1620 may comprise extracting features from each of the medical scan image 905 and the approved local contours, the features being derived from intensities, intensity gradients and/or local context.

Step 1640 may then comprise optimising internal parameters of the algorithm to provide a match between the estimated set of universal contours generated by the algorithm and the set of the globally approved universal contours. Step 1640 may comprise calculating a cost function, the cost function evaluating the set of differences between the estimated set of universal contours and the set of globally approved universal contours. The cost function is then used to estimate an extent of the match, and the cost function is then minimised.

The trained model, may be used to estimate sets of universal contours for medical scan images from a research project conducted at multiple institutions. The trained model may then be used to populate a single universal atlas database 901 with new atlases, the single universal atlas database 901 being accessible remotely by the multiple institutions.

A computer program product in accordance with the invention has executable code for a method in accordance with the invention. The invention may be implemented in a computer program for running on a computer system, at least including code portions for performing steps of a method according to the invention when run on a programmable apparatus, such as a computer system or enabling a programmable apparatus to perform functions of a device or system according to the invention.

The computer program may be stored internally on a tangible and non-transitory computer readable storage medium or transmitted to the computer system via a computer readable transmission medium. The computer system may for instance include at least one processing unit such as a CPU or ASIC, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims. Those skilled in the art will recognize that boundaries between the above described operations are merely illustrative. The multiple operations may be combined into a single operation, a single operation may be distributed in additional operations and operations may be executed at least partially overlapping in time. However, other modifications, variations and alternatives are also possible. The specifications and drawings are, accordingly, to be regarded in an illustrative. In the claims, any reference signs placed between parentheses shall not be construed as limiting the claim.

The invention claimed is:

1. A method of generating an atlas for a global standardised atlas database, the method comprising:
   a) providing a medical scan image;
   b) performing a universal auto-contouring operation using the global standardised atlas database on the medical scan image, to generate a set of universal contours for the medical scan image;
   c) performing an institution specific auto-contouring customisation operation on the medical scan image, to generate a set of local contours for the medical scan image, approval or editing of the set of local contours, and adding a local atlas to the local atlas database;
   d) standardising the set of local contours, using a trained model to compensate for biases in the set of local contours, thereby creating a set of standardised global contours for the medical scan image;
   and adding an atlas to the global standardised atlas database, the atlas comprising the medical scan image and the set of standardised global contours for the medical scan image.

2. The method of claim 1, further comprising:
   The institution specific auto-contouring customisation operation comprising adaptation of the universal contours to local guidelines of a local institution; and
   the local institution providing the medical scan image and the local atlas database, and performing the universal auto-contouring operation and the institution specific auto-contouring customisation operation.

3. The method of claim 1,
   wherein the local atlas added to the local atlas database comprising the medical scan image and the set of local contours, after the approval or editing.

4. The method of claim 1, further comprising:
   repeating the method for a plurality of medical scan images, thereby creating a set of standardised global contours for each medical scan image; and
   adding, to the global standardised atlas database, an atlas for each of the plurality of medical scan images, each atlas comprising the medical scan image and the set of standardised global contours for the medical scan image.

5. The method of claim 1, further comprising:
adding the first atlas to a second local database, the second local database being available only to the local institution.

6. The method of claim 1, further comprising:
using the set of universal contours in a training step, the training step comprising comparing the set of universal contours to the set of local contours, in order to further optimise the trained model that performs the standardising of the set of local contours.

7. The method of claim 1, further comprising:
performing the universal auto-contouring operation on the medical scan image with input from the global standardised atlas database.

8. The method of claim 7, wherein:
the input from the global standardised atlas database to the universal auto-contouring operation comprises a stored atlas from the global standardised atlas database.

9. The method of claim 8, wherein:
the input from the global standardised atlas database to the universal auto-contouring operation comprises a set of variations between a plurality of atlases stored in the global standardised atlas database.

10. The method of claim 1, further comprising:
performing the institution specific auto-contouring customisation operation on the medical scan image with input from a local atlas database.

11. The method of claim 10, wherein:
the input from the local atlas database to the institution specific auto-contouring customisation operation comprises a local atlas from the local atlas database.

12. The method of claim 1, wherein the universal auto-contouring operation comprises at least one from, or a combination of:
an atlas-based operation; a shape/appearance model; a machine learning approach; or a deep learning algorithm.

13. An apparatus for generating an atlas for a global standardised atlas database, the apparatus comprising:
a memory, the memory configured to store a medical scan image;
a processor, the processor configured to:
a) perform a universal auto-contouring operation using the global standardised atlas database on the medical scan image, thereby generating a set of universal contours for the medical scan image;
b) perform an institution specific auto-contouring customisation operation on the medical scan image, thereby generating a set of local contours for the medical scan image; approval or editing of the set of local contours, adding a local atlas to the local atlas database:
c) standardise the set of local contours, using a trained model to compensate for biases in the set of local contours, thereby creating a set of standardised global contours for the medical scan image, and adding an atlas to the global standardised atlas database, the atlas comprising the medical scan image and the set of standardised global contours for the medical scan image.

* * * * *